(12) United States Patent
Kelly et al.

(10) Patent No.: US 10,758,394 B2
(45) Date of Patent: Sep. 1, 2020

(54) POWERED ORTHOTIC DEVICE AND METHOD OF USING SAME

(71) Applicant: Myomo, Inc., Cambridge, MA (US)

(72) Inventors: Stephen R. Kelly, Manchester, MA (US); Gene Tacy, Windham, NH (US); Samuel Kesner, Arlington, MA (US); Andrew Harlan, Somerville, MA (US)

(73) Assignee: Myomo, Inc., Cambridge, MA (US)

( * ) Notice: Subject to any disclaimer, the term of this patent is extended or adjusted under 35 U.S.C. 154(b) by 1010 days.

(21) Appl. No.: 15/183,279

(22) Filed: Jun. 15, 2016

(65) Prior Publication Data

US 2016/0287422 A1    Oct. 6, 2016

Related U.S. Application Data

(60) Provisional application No. 62/175,765, filed on Jun. 15, 2015.

(51) Int. Cl.
*A61H 1/02* (2006.01)
*A61F 5/01* (2006.01)

(52) U.S. Cl.
CPC ............ *A61F 5/013* (2013.01); *A61F 5/0127* (2013.01); *A61H 1/02* (2013.01); *A61F 2005/0155* (2013.01); *A61F 2005/0169* (2013.01)

(58) Field of Classification Search
CPC .............. A61F 5/013; A61F 5/0127; A61F 2005/0169; A61F 2005/0155; A61H 1/02;
(Continued)

(56) References Cited

U.S. PATENT DOCUMENTS

| 3,631,542 A | 1/1972 | Potter ............................ 3/1.1 |
| 4,030,141 A | 6/1977 | Graupe ........................... 3/1.1 |

(Continued)

FOREIGN PATENT DOCUMENTS

| JP | H8-687 A | 1/1996 | ............ A61H 1/02 |
| JP | 2005-253650 A | 9/2005 | ............ A61H 3/00 |

(Continued)

OTHER PUBLICATIONS

Abul-Haj et al., "Functional Assessment of Control Systems for Cybernetic Elbow Prostheses—Part II: Application of the Technique," IEEE Transactions on Biomedical Engineering, vol. 37, No. 11, pp. 1037-1047, Nov. 1990.

(Continued)

*Primary Examiner* — Quang D Thanh
(74) *Attorney, Agent, or Firm* — Sunstein LLP

(57) ABSTRACT

A powered orthotic device for use with a limb having at least two joints includes at least two brace sub-assemblies. The first brace sub-assembly includes a first powered actuator assembly that receives a first sensor signal from an electromyographic sensor. The first powered actuator assembly applies a first force for driving sections positioned with respect to a first joint to move relative to one another. The second brace sub-assembly includes a second powered actuator assembly that is configured to receive a second sensor signal from a sensor selected from a group consisting of an electromyographic sensor, an inertial measurement unit, and combinations thereof. The second powered actuator assembly applies a second force for driving sections positioned with respect to a second joint to move relative to one another. The second force is based on the first sensor signal or the second sensor signal.

22 Claims, 28 Drawing Sheets

(58) Field of Classification Search
CPC .. A61H 1/0277; A61H 1/008; A61H 2230/08; A61H 2230/085; A61H 2230/10; A61H 2230/105; A61H 2230/60; A61H 2230/605; A61B 5/1116

See application file for complete search history.

(56) References Cited

U.S. PATENT DOCUMENTS

| | | | |
|---|---|---|---|
| 4,209,860 A | 7/1980 | Graupe | 3/1.1 |
| 4,650,492 A | 3/1987 | Barkhordar et al. | 623/24 |
| 4,685,925 A | 8/1987 | Childress et al. | 623/25 |
| 5,112,296 A | 5/1992 | Beard et al. | 602/28 |
| 5,282,460 A | 2/1994 | Boldt | 128/25 R |
| 5,466,213 A | 11/1995 | Hogan et al. | 601/33 |
| 5,682,327 A | 10/1997 | Telepko | 364/550 |
| 5,685,830 A | 11/1997 | Bonutti | 602/16 |
| 5,800,561 A | 9/1998 | Rodriguez | 623/26 |
| 5,853,005 A | 12/1998 | Scanlon | 128/662.03 |
| 5,888,212 A | 3/1999 | Petrofsky et al. | 623/24 |
| 5,888,213 A | 3/1999 | Sears et al. | 625/24 |
| 5,951,499 A | 9/1999 | Saringer et al. | 601/33 |
| 5,954,621 A | 9/1999 | Joutras et al. | 482/114 |
| 5,980,435 A | 11/1999 | Joutras et al. | 482/114 |
| RE37,209 E | 6/2001 | Hensley et al. | 602/26 |
| 6,379,393 B1 | 4/2002 | Mavroidis et al. | 623/25 |
| 6,532,383 B2 | 3/2003 | Maloney et al. | 600/546 |
| 6,599,255 B2 | 7/2003 | Zhang | 600/587 |
| 6,616,579 B1 | 9/2003 | Reinbold et al. | 482/91 |
| 6,660,042 B1 | 12/2003 | Curcie et al. | 623/24 |
| 6,676,612 B1 | 1/2004 | Beny et al. | 601/5 |
| 6,743,187 B2 | 6/2004 | Solomon et al. | 600/587 |
| 6,821,259 B2 | 11/2004 | Rahman et al. | 601/5 |
| 6,880,487 B2 | 4/2005 | Reinkensmeyer et al. | 119/700 |
| 6,944,496 B2 | 9/2005 | Jeong et al. | 600/546 |
| 6,966,882 B2 | 11/2005 | Horst | 601/5 |
| 6,969,365 B2 | 11/2005 | Scorvo | 602/16 |
| 7,182,738 B2 | 2/2007 | Bonutti et al. | 601/5 |
| 8,585,620 B2 | 11/2013 | McBean et al. | 601/5 |
| 8,926,534 B2 | 1/2015 | McBean et al. | 601/5 |
| 9,398,994 B2 | 7/2016 | McBean et al. | |
| 2002/0169402 A1 | 11/2002 | Hatton et al. | 602/26 |
| 2002/0183673 A1 | 12/2002 | Naft et al. | 602/16 |
| 2003/0023195 A1 | 1/2003 | Rahman et al. | 602/20 |
| 2003/0064869 A1 | 4/2003 | Reinkensmeyer et al. | 482/100 |
| 2003/0120183 A1 | 6/2003 | Simmons | 600/595 |
| 2004/0082885 A1* | 4/2004 | Culhane | A61H 1/0277 601/5 |
| 2004/0106881 A1* | 6/2004 | McBean | A61B 5/04888 601/5 |
| 2005/0006980 A1 | 1/2005 | Horst | 310/309 |
| 2006/0004307 A1 | 1/2006 | Horst | 601/5 |
| 2006/0052731 A1 | 3/2006 | Shimada et al. | 602/5 |
| 2006/0064044 A1 | 3/2006 | Schmehl | 601/34 |
| 2006/0069336 A1 | 3/2006 | Krebs et al. | 602/28 |
| 2006/0130594 A1 | 6/2006 | Ikeuchi | 73/862.08 |
| 2006/0149338 A1 | 7/2006 | Flaherty et al. | 607/49 |
| 2007/0191743 A1 | 8/2007 | McBean et al. | 601/5 |
| 2008/0071386 A1* | 3/2008 | McBean | A61F 5/0127 623/25 |
| 2008/0077057 A1* | 3/2008 | Peles | A61H 1/0277 601/5 |
| 2008/0139968 A1 | 6/2008 | Endo et al. | 600/595 |
| 2008/0161937 A1* | 7/2008 | Sankai | A61H 3/008 623/25 |
| 2008/0234608 A1 | 9/2008 | Sankai | 601/5 |
| 2010/0201804 A1* | 8/2010 | Pellegrino | G01N 21/8806 348/92 |
| 2010/0217163 A1* | 8/2010 | Sankai | B25J 9/0006 601/5 |
| 2012/0179075 A1* | 7/2012 | Perry | B25J 9/0006 601/33 |
| 2014/0172166 A1* | 6/2014 | Kim | B25J 3/04 700/259 |
| 2014/0277582 A1* | 9/2014 | Leuthardt | A61B 5/04085 623/25 |
| 2015/0148728 A1* | 5/2015 | Sallum | A61F 5/10 602/22 |
| 2016/0051388 A1* | 2/2016 | Goldfarb | A61F 5/013 602/16 |
| 2016/0128890 A1* | 5/2016 | LaChappelle | A61H 3/00 623/30 |

FOREIGN PATENT DOCUMENTS

| | | | | |
|---|---|---|---|---|
| JP | 2006-087533 A | 4/2006 | | A61H 3/00 |
| JP | 2006-167313 A | 6/2006 | | A61H 3/00 |
| WO | WO 2004/107085 A2 | 12/2004 | | |
| WO | WO 2006/064657 A1 | 6/2006 | | A61H 3/00 |
| WO | WO 2013/036925 A2 | 3/2013 | | A61F 5/10 |

OTHER PUBLICATIONS

Benjuya et al., "Hybrid Arm Orthosis," Journal of Prosthetics and Orthotics, vol. 2, No. 2, pp. 155-163, 1990.

Benjuya et al., "Myoelectric Hand Orthosis," Journal of Prosthetics and Orthotics, vol. 2, No. 2, pp. 149-152, 1990.

Bowen et al., "Surface EMG and Motor Control of the Upper Extremity in Muscular Dystrophy: A Pilot Study," Proceedings of the 23$^{rd}$ Annual International Conference of the IEEE Engineering in Medicine and Biology Society, vol. 4, pp. 289-290, Oct. 25-28, 2001.

Brown et al., "The Exoskeleton Glove for Control of Paralyzed Hands," IEEE International Conference on Robotics and Automation, vol. 1, pp. 642-647, May 2-6, 1993.

Downes et al., "Distributed Control of an Electrically Powered Hip Orthosis," International Conference on Control, Publication No. 389, pp. 24-30, Mar. 21-24, 1994.

Fukuda et al., "EMG-based Human-Robot Interface for Rehabilitation Aid," Proceedings of the 1998 IEEE International Conference on Robotics and Automation, vol. 4, pp. 3492-3497, May 20, 1998.

Harwin et al., "A Review of Design Issues in Rehabilitation Robotics with Reference to North American Research," IEEE Transactions on Rehabilitation Engineering, vol. 3, No. 1, pp. 3-13, Mar. 1995.

Harwin et al., "Criteria for Interfacing and Control of a Powered Upper Extremity Orthosis," Journal of Rehabilitation Research and Development, Supplemental Progress Reports, vol. 33, 2 pages, Jun. 1996.

Homma et al., "An Upper Limb Motion Assist System: Experiments with arm models," Proceedings of the 1998 IEEE/RSJ International Conference on Intelligent Robots and Systems, vol. 3, pp. 758-763, Oct. 17, 1998.

Johnson et al., "Development of a Mobility Assist for the Paralyzed, Amputee, and Spastic Patient," Proceedings of the 1996 Fifteenth Southern Biomedical Engineering Conference, pp. 67-70, Mar. 29-31, 1996.

Kawamoto et al., "Comfortable Power Assist Control Method for Walking Aid by HAL-3," IEEE International Conference on Systems, Man, and Cybernetics, vol. 7, 6 pages, Oct. 6-9, 2002.

Kawamura et al., "A Design of Motion-Support Robots for Human Arms using Hexahedron Rubber Actuators," Proceedings of the 1997 IEEE/RSJ International Conference on Intelligent Robots and Systems, vol. 3, pp. 1520-1526, Sep. 11, 1997.

Kazerooni, "Stability and Performance of Robotic Systems Worn by Humans," Proceedings of the 1990 IEEE International Conference on Robotics and Automation, vol. 1, pp. 558-563, May 13-18, 1990.

Kiguchi et al., "An Exoskeletal Robot for Human Elbow Motion Support—Sensor Fusion, Adaptation, and Control," IEEE Transactions on Systems, Man, and Cybernetics—Part B: Cybernetics, vol. 31, No. 3, pp. 353-361, Jun. 2001.

Kiguchi et al., "An Exoskeleton System for Elbow Joint Motion Rehabilitation," Proceedings of the 2003 IEEE/ASME International Conference on Advanced Intelligent Mechatronics (AIM 2003), vol. 2, pp. 1228-1233, Jul. 20-24, 2003.

(56) References Cited

OTHER PUBLICATIONS

Krebs et al., "Robot-Aided Neuro-Rehabilitation in Stroke: Three-Year Follow-Up," International Conference on Rehabilitation Robotics, Stanford, CA, pp. 34-41, 1999.
Krebs et al., "Increasing productivity and quality of care: Robot-aided neuro-rehabilitation," Journal of Rehabilitation Research and Development, vol. 37, No. 6, 17 pages, Nov./Dec. 2000.
Krebs et al., "Robot-Aided Neurorehabilitation," IEEE Transactions on Rehabilitation Engineering, vol. 6, No. 1, pp. 75-87, Mar. 1998.
Lee et al., "Power Assist Control for Walking Aid with HAL-3 Based on EMG and Impedance Adjustment around Knee Joint," Proceedings of the 2002 IEEE/RSJ International Conference on Intelligent Robots and Systems, pp. 1499-1504, Oct. 2002.
Lee et al., "A New Exoskeleton-type Masterarm with Force Reflection: Controller and Integration," Proceedings of the 1999 IEEE/RSJ International Conference on Intelligent Robots and Systems, vol. 3, pp. 1438-1443, Oct. 17-21, 1999.
Lum et al., "A Robotic System for Upper-Limb Exercises to Promote Recovery of Motor Function Following Stroke," ICORR '99: International Conference on Rehabilitation Robotics, Stanford, CA, pp. 235-239, 1999.
Lum et al., "Quantification of Force Abnormalities During Passive and Active-Assisted Upper-Limb Reaching Movements in Post-Stroke Hemiparesis," IEEE Transactions on Biomedical Engineering, vol. 46, No. 6, pp. 652-662, Jun. 1999.
Lum et al., "Robotic Assist Devices for Bimanual Physical Therapy: Preliminary Experiments," IEEE Transactions on Rehabilitation Engineering, vol. 1, No. 3, pp. 185-191, Sep. 1993.
Morita et al., "Basic Study on Rehabilitation Support System for Upper Limb Motor Function," IEEE 7th International Workshop on Advanced Motion Control, pp. 127-132, Jul. 3-5, 2002.
Parsons et al., "An Adaptable User Interface and Controller for a Rehabilitation Robotic Arm," 8th International Conference on Advanced Robotics Proceedings, pp. 919-923, Jul. 7-9, 1997.
Popovic et al., "Hybrid Assistive System—The Motor Neuroprosthesis," IEEE Transactions on Biomedical Engineering, vol. 36, No. 7, pp. 729-737, Jul. 1989.
Rabischong et al., "Control and Command of a Six Degrees of Freedom Active Electrical Orthosis for Paraplegic Patient," IEEE International Workshop on Intelligent Robots and Systems, vol. 1, pp. 987-991, Jul. 3-6, 1990.
Reinkensmeyer et al., "Guidance-Based Quantification of Arm Impairment Following Brain Injury: A Pilot Study," IEEE Transactions on Rehabilitation Engineering, vol. 7, No. 1, 11 pages, Mar. 1999.
Romilly et al., "A Functional Task Analysis and Motion Simulation for the Development of a Powered Upper-Limb Orthosis," IEEE Transactions on Rehabilitation Engineering, vol. 2, No. 3, pp. 119-129, Sep. 1994.
Rosen et al., "A Myosignal-Based Powered Exoskeleton System," IEEE Transaction on Systems, Man, and Cybernetics—Part A: Systems and Humans, vol. 31, No. 3, pp. 210-222, May 2001.
Seliktar et al., "Evaluation of Functional Capabilities of People with Muscular Dystrophy as Potential Users of Powered Orthoses," American Society of Mechanical Engineers, Summer Bioengineering Conference, 2 pages, Jun. 16-20, 1999.
Shibata et al., "A Study on Self-powered Ankle Foot Orthosis," Japan Society of Mechanical Engineering, Dynamics and Design Conference, 5 pages, Aug. 6-9, 2006.
Timoszyk et al., "Robot-Assisted Locomotion Training after Spinal Cord Injury: Comparison of Rodent Stepping in Virtual and Physical Treadmill Environments," IEEE International Conference, 15 pages, 1990.
Triolo et al., "The Theoretical Development of a Multichannel Time-Series Myoprocessor for Simultaneous Limb Function Detection and Muscle Force Estimation," IEEE Transactions on Biomedical Engineering, vol. 36, No. 10, pp. 1004-1017, Oct. 1989.
Umetani et al., "Skil Mate," Wearable Exoskelton Robot, IEEE International Conference on Systems, Man, and Cybernetics, vol. 5, pp. 984-988, Oct. 12-15, 1999.
Wiegner et al., "Design of a Triceps Orthosis for C5/C6 Quadriplegics," Proceedings of the Annual International Conference of the IEEE Engineering in Medicine and Biology Society, vol. 14, pp. 1485-1486, Nov. 1992.
Wu et al., "A Study of Neuromuscular-like Control in Rehabilitation Robot," Proceedings of the 1996 IEEE International Conference on Robotics and Automation, vol. 4, pp. 1178-1183, Apr. 22-28, 1996.
Zardoshti-Kermani et al., "EMG Feature Evaluation for Movement Control of Upper Extremity Prostheses," IEEE Transactions on Rehabilitation Engineering, vol. 3, No. 4, pp. 324-333, Dec. 1995.
International Searching Authority, International Search Report and Written Opinion for PCT/US2007/078900, dated May 20, 2008, 16 pages.
International Searching Authority, International Search Report and Written Opinion for PCT/US2016/037607, dated Oct. 21, 2016, 10 pages.

\* cited by examiner

CO = Command Output to actuation system
$OS_i$ = Output Signal (from particular relationship. Example: $OS_{EMGi}$).

(1) $CO = A(OS_{EMGi}) + B \cdot (OS_{position}) - C \cdot (OS_{elapsed\ time})$;

where A, B, C are constants.

(2) $CO = S_{in}(OS_{position}) + \dfrac{(OS_{EMGi})^2}{2} - OS_{current}$ (3) If $OS_{time} \leq D$, then $CO = E \cdot OS_{EMGi}$ If $OS_{time} > D$, then $CO = E \cdot OS_{EMGi} - F \cdot OS_{time}$;

where D, E, F are constants.

(4) If $OS_{EMGi} \leq G$, and $OS_{temp} \leq H$, and $|OS_{position}| \leq I$, then $CO = OS_{EMGi}$ ELSE, $CO = 0$;
where G, H, I are constants.

*Fig. 19*

POWERED ORTHOTIC DEVICE AND METHOD OF USING SAME

CROSS-REFERENCE TO RELATED APPLICATIONS

The present application claims the benefit of U.S. Provisional Patent Application No. 62/175,765 filed Jun. 15, 2015. The disclosure of this provisional application is incorporated by reference herein in its entirety.

TECHNICAL FIELD

The disclosure generally relates to orthotic devices and, more particularly, the disclosure relates to powered orthotic devices and methods of using the same for rehabilitation or functional aids.

BACKGROUND

Stroke, brain injury, and other neuromuscular trauma survivors are often left with hemiparesis, or severe weakness in certain parts of the body. The result can be impaired or lost function in one or more limbs. It has been shown that people can rehabilitate significantly from many of the impairments following such neurological traumas. Further, it has been shown that rehabilitation is much more effective, and motor patterns re-learned more quickly, if the rehabilitative exercise regime includes the execution of familiar and functional tasks. Following neuromuscular trauma, however, the control or strength in the afflicted limb or limbs may be so severely diminished that the patient may have difficulty (or be unable) performing constructive, functional rehabilitation exercises without assistance.

SUMMARY OF THE EMBODIMENTS

One embodiment of the invention includes a powered orthotic device for use with a limb having at least two joints. The device includes a brace system including at least two brace sub-assemblies. The first brace sub-assembly is operative with respect to a first one of the joints and a second brace sub-assembly is operative with respect to a second one of the joints. The first brace sub-assembly includes a first section and a second section, and the first section and the second section are configured for relative motion with respect to one another about the first one of the joints. The first brace sub-assembly is configured to removably attach its first section and its second section to a corresponding limb segment. The first brace sub-assembly includes a first powered actuator assembly that is configured to receive a first sensor signal from an electromyographic sensor, and that is also mechanically coupled to the first brace sub-assembly so as to apply a first force for driving the first and second sections of the first brace sub-assembly to move relative to one another. The first force based on the first sensor signal.

The second brace sub-assembly includes a first section and a second section, and the first section and the second section are configured for relative motion with respect to one another about the second one of the joints. The second brace sub-assembly is configured to removably attach its first section and its second section to a corresponding limb segment. The second powered actuator assembly is configured to receive a second sensor signal from a sensor selected from a group consisting of an electromyographic sensor, an inertial measurement unit, and combinations thereof. The second powered actuator assembly is also configured to be mechanically coupled to the second brace sub-assembly so as to apply a second force for driving the first and second sections of the second brace sub-assembly to move relative to one another. The second force is based on the first sensor signal or the second sensor signal. The brace system and the first and second actuator assemblies form a wearable component.

In some embodiments, the first brace sub-assembly includes the electromyographic sensor. In various embodiments, the second brace sub-assembly includes the sensor. The first brace sub-assembly may include an inertial measurement unit that outputs a third sensor signal, and the first force may be based on the first sensor signal and the third sensor signal.

In some embodiments, the second section of the first brace sub-assembly and the first section of the second brace sub-assembly may be the same section. In some of these embodiments, the first brace sub-assembly may be configured to removably attach its second section to a forearm, and the second brace sub-assembly may be configured to removably attach its first section to a forearm and its second section to a hand. The first force may be based additionally on the second sensor signal. The second force may be based on the first and second sensor signals.

The second actuator assembly may be configured to be positioned along the second brace sub-assembly and proximate to the second one of the joints. The second actuator assembly may be configured to be positioned on the second brace sub-assembly such that the second actuator assembly is positioned remotely from the second one of the joints when the device is removably attached to a user. The first actuator assembly may include a motor in a housing and a drive assembly coupled to the motor as well as the first and second sections of the first brace sub-assembly. The motor may be positioned proximate to a juncture between the first and second sections of the first brace sub-assembly. The juncture may be proximate to an elbow or a wrist when the first brace sub-assembly is configured to be removably attached to a forearm.

The second actuator assembly may include a motor in a housing and a drive assembly coupled to the motor as well as the first and second sections of the second brace sub-assembly. The motor may be positioned proximate to a juncture between the first and second sections of the second brace sub-assembly. The juncture may be proximate to a finger joint when the second brace sub-assembly is configured to be removably attached to a hand.

The second actuator assembly may be a linear actuator assembly or a rotary actuator assembly. The second actuator assembly may be a cable-based actuator assembly or a tendon-based actuator assembly. The first actuator assembly and the second actuator assembly may communicate regarding the first force applied to the first brace sub-assembly and the second force applied to the second brace sub-assembly.

In some embodiments, the device includes a controller system in communication with the first and second brace sub-assemblies. The controller system may include a processing system that receives the first and second sensor signals and generates output signals to the first and second actuator assemblies. The controller system may include a user interface through which a user interacts with the device. The controller system may automatically self-adjust one or more parameters selected from the group consisting of brace strength, system gains, system sensitivities, virtual spring parameters, EMG threshold values, maximum and minimum torques, operational range of motion, damping parameters, user feedback modes, data logging parameters, and any combination thereof. The controller system may be coupled to the second brace sub-assembly via a cable or wireless system. The controller system may be coupled to the Internet, so that the device is able to communicate with a remotely located computing device. The controller system may include a data management system for storing data received from the device, from a user or both. The wearable component may include a battery coupled to the first and second powered actuator assemblies.

BRIEF DESCRIPTION OF THE DRAWINGS

The foregoing features of embodiments will be more readily understood by reference to the following detailed description, taken with reference to the accompanying drawings, in which:

FIG. 19 shows an exemplary control algorithm according to exemplary embodiments of the present invention;

DETAILED DESCRIPTION OF SPECIFIC EMBODIMENTS

Figure 1:
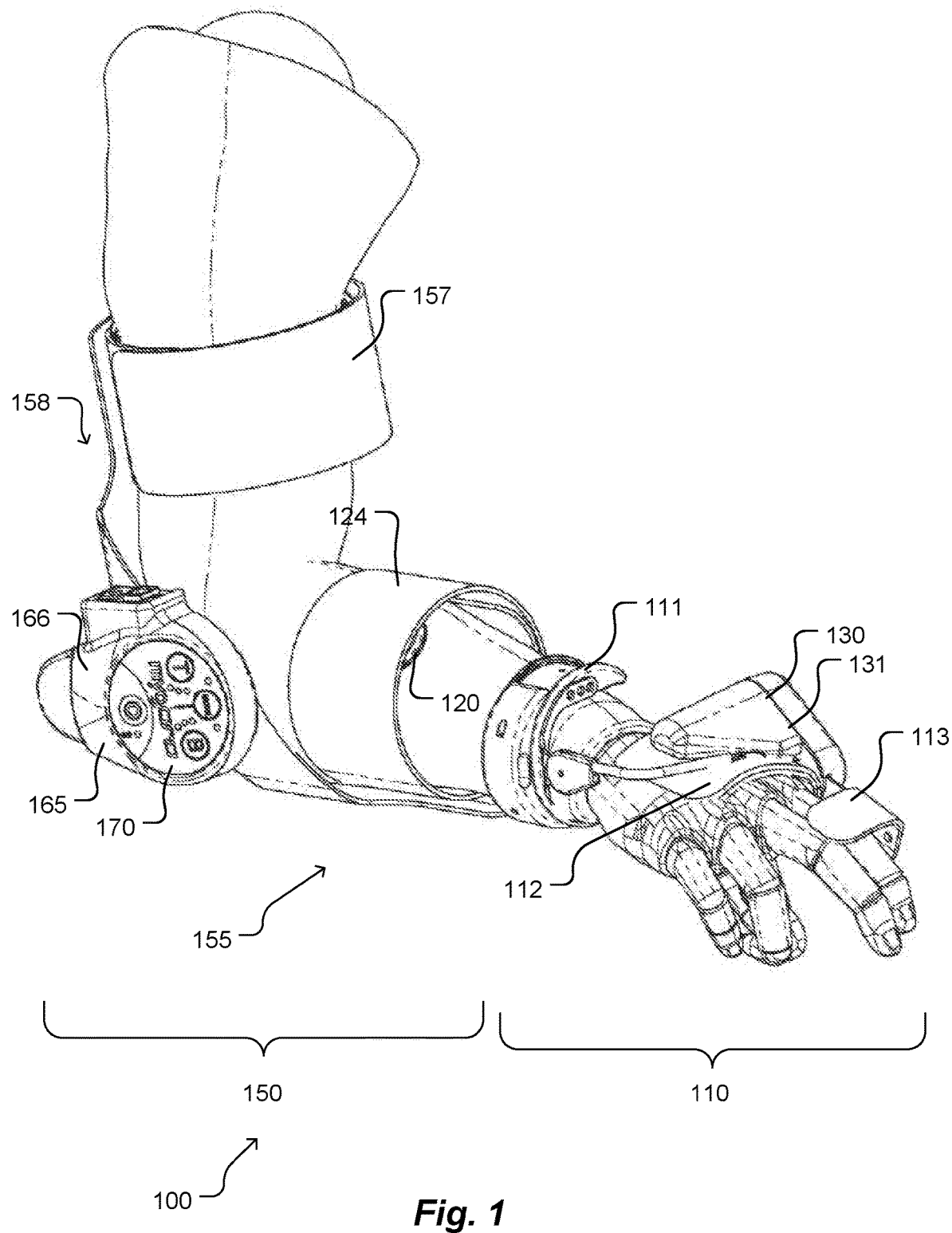
FIG. 1 shows an isometric view of a powered orthotic device including a brace system with two brace sub-assemblies that are removably attached to a limb of a subject.

Definitions. As used in this description and the accompanying claims, the following terms shall have the meanings indicated, unless the context otherwise requires:

An "orthotic device" is a support or brace for weak or ineffective joints or muscles. An orthotic device is worn over existing body parts to support and/or restore function to a weakened or malformed body part.

A "limb" is an arm or a leg, wherein a portion, up to the whole thereof, of the arm or leg optionally includes a prosthesis.

A "prosthesis" is an artificial device to replace a missing part of the body.

A "limb segment" is a portion of a limb.

A "joint" is a coupling between adjacent limb segments.

"User" is defined by context and refers to anyone who is interacting with the device at the moment. For example, user includes the patient or wearer of the device while the device is functioning, and a clinician, trained professional, or anyone else who is interacting with the device at the moment via the user interface.

People afflicted with neuromuscular conditions often exhibit diminished fine and gross motor skills. For example, even if a person retains symmetric control over a joint, the person may be left with reduced control over muscle groups on opposite sides of the joint. Not only may the person be incapable of achieving the full range of motion that the joint would normally permit, the person may also be incapable of controlling the joint so that the associated limb segments exert desired amounts of force on surrounding objects. For example, if the person wants to pinch an object between his or her index finger and thumb, the person must use at least the adductor pollicis, first dorsal interosseous, and flexor pollicis brevis muscles to position the fingers around the object and then grasp accordingly. When the person cannot move his or her fingers to the proper positions, or apply the required force, the person will be unable to hold objects.

In another example, a person may be capable of only asymmetric control of a particular joint. In these situations, the person may be capable of flexing or extending the joint, but not both. The user may be able to control the muscle group responsible for flexion about the joint, but his or her control over the muscle group responsible for extension may be impaired. Similarly, the opposite may be true, e.g., the user may have control in the extension direction, but not the flexion direction. As an example, the task of reaching by extending an arm may require relaxing the flexors (e.g., biceps, brachioradialis) and allowing tension in the extensors (e.g., triceps) to dominate. However, if a person cannot exert his or her triceps or release a hyperactive bicep, the person will fail to complete the task.

Embodiments of the present invention enable their users to achieve more natural gross and fine motion. When users wear the powered orthotic devices described herein, the devices enhance the users' functional capacities. In particular, various embodiments of the present invention may use control algorithms that mimic, in real time, the natural patterns of motion and force about multiple joints, even in the absence of the user's impaired ability to control one or more of the major muscle groups that effect force and motion about the joint. The powered orthotic devices each include a brace system with at least two brace sub-assemblies, each of which attaches to two of the user's limb segments and operates with respect to a different joint. At least one of the brace sub-assemblies includes at least one electromyographic (EMG) sensor. When the user removably attaches the device to his or her limb, at least one EMG sensor becomes coupled to one of the user's muscle groups. As the user attempts to move a limb, the EMG sensor detects activity in the user's muscles. Based on the outputs of at least one sensor, the device applies a torque to one, or both, of the brace sub-assemblies to assist the user's motion.

In some embodiments, at least one of the brace sub-assemblies of the orthotic device includes an inertial measurement unit (IMU). The orthotic device may determine the torque to apply to at least one of the brace sub-assemblies based on the outputs of the IMU and EMG sensor(s). As a result, the combination of the IMU and EMG sensor(s) may enable the orthotic device to provide more refined assistance to the user than devices that rely solely on the EMG sensor(s).

Exemplary Embodiments of the Powered Orthotic Device

Figure 2:
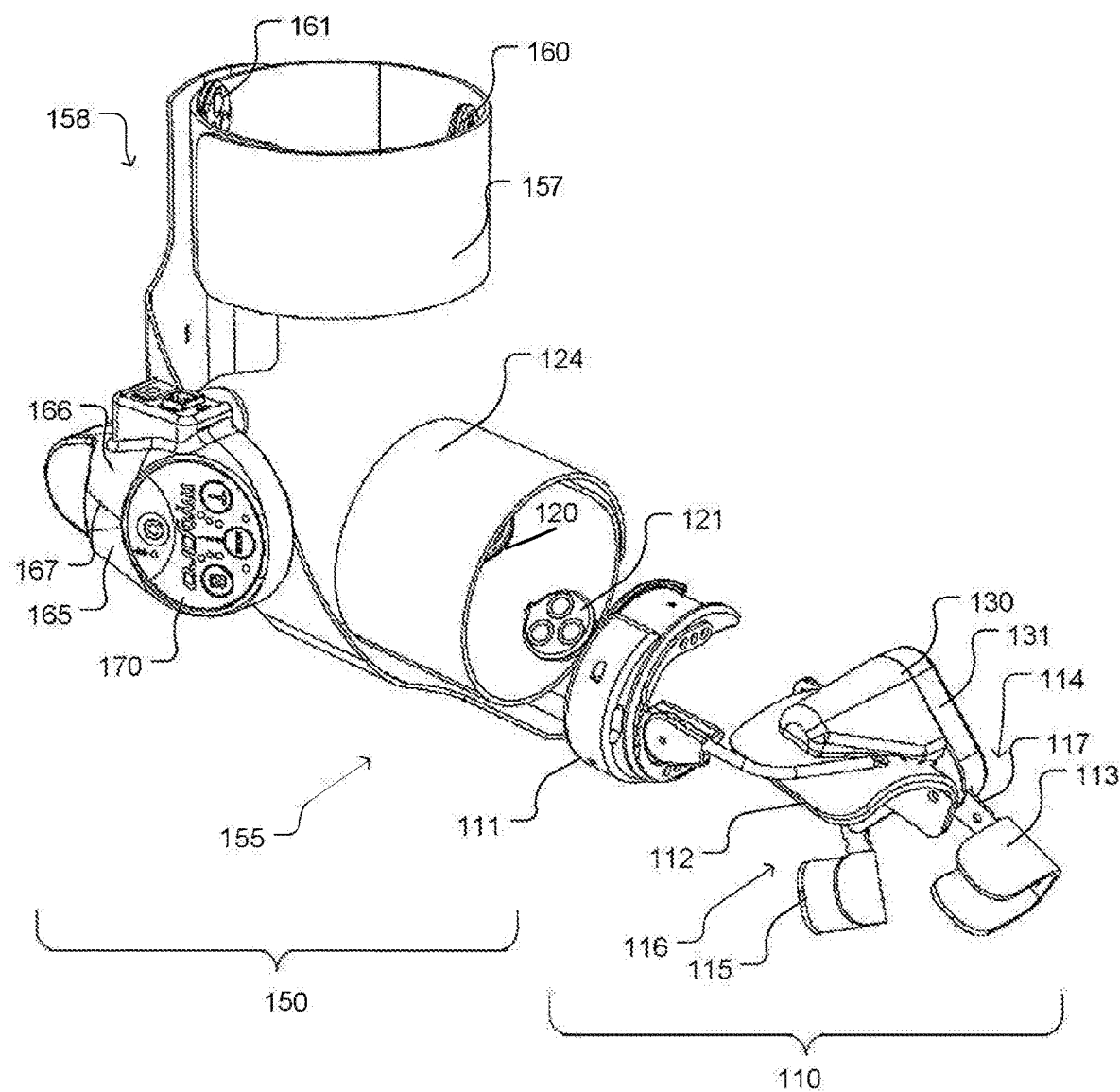
FIG. 2 shows the powered orthotic device of FIG. 1, as detached from the limb.
Figure 3:
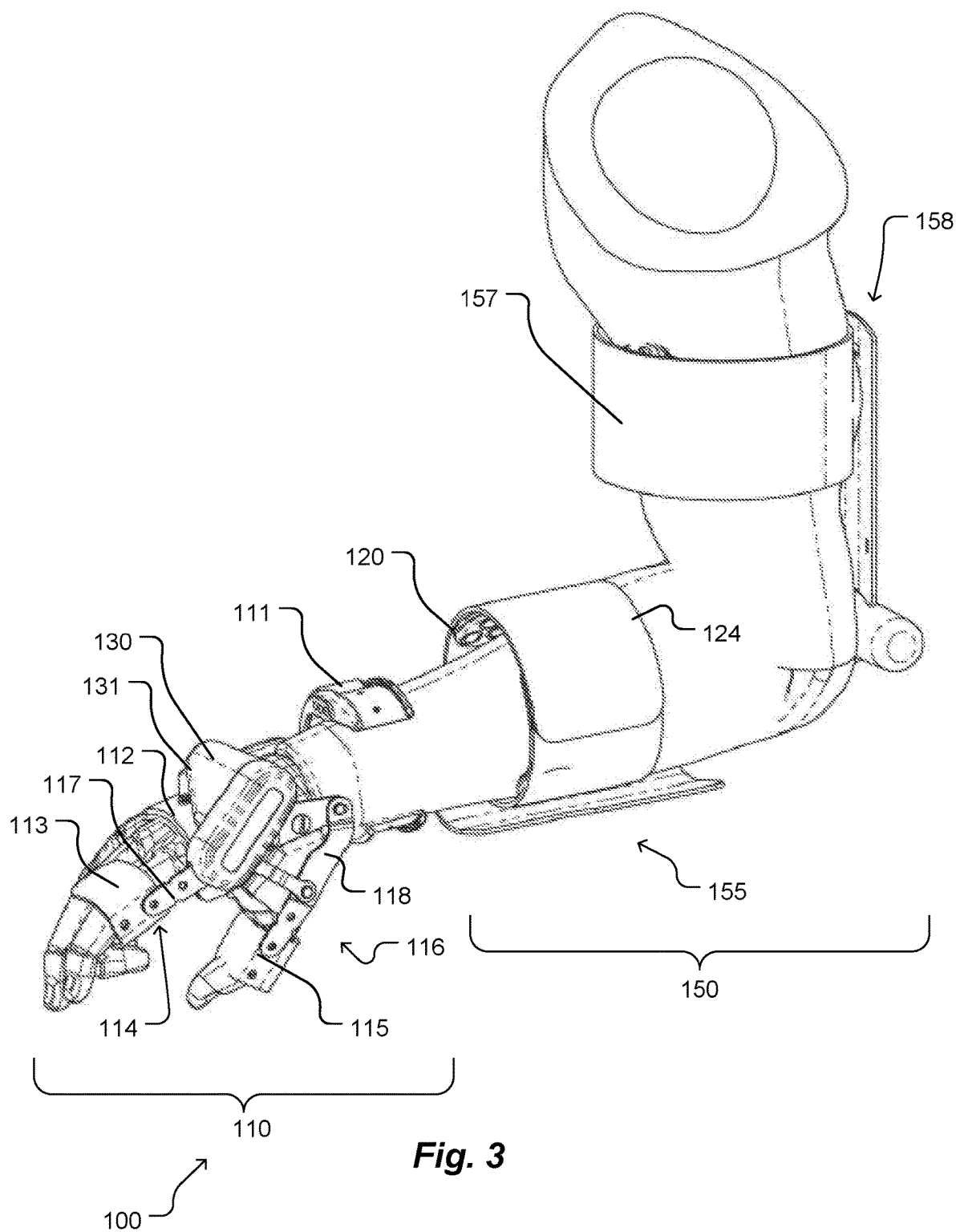
FIG. 3 shows an isometric view of a powered orthotic device including a brace system with two brace sub-assemblies that are removably attached to a limb of a subject.
Figure 4:
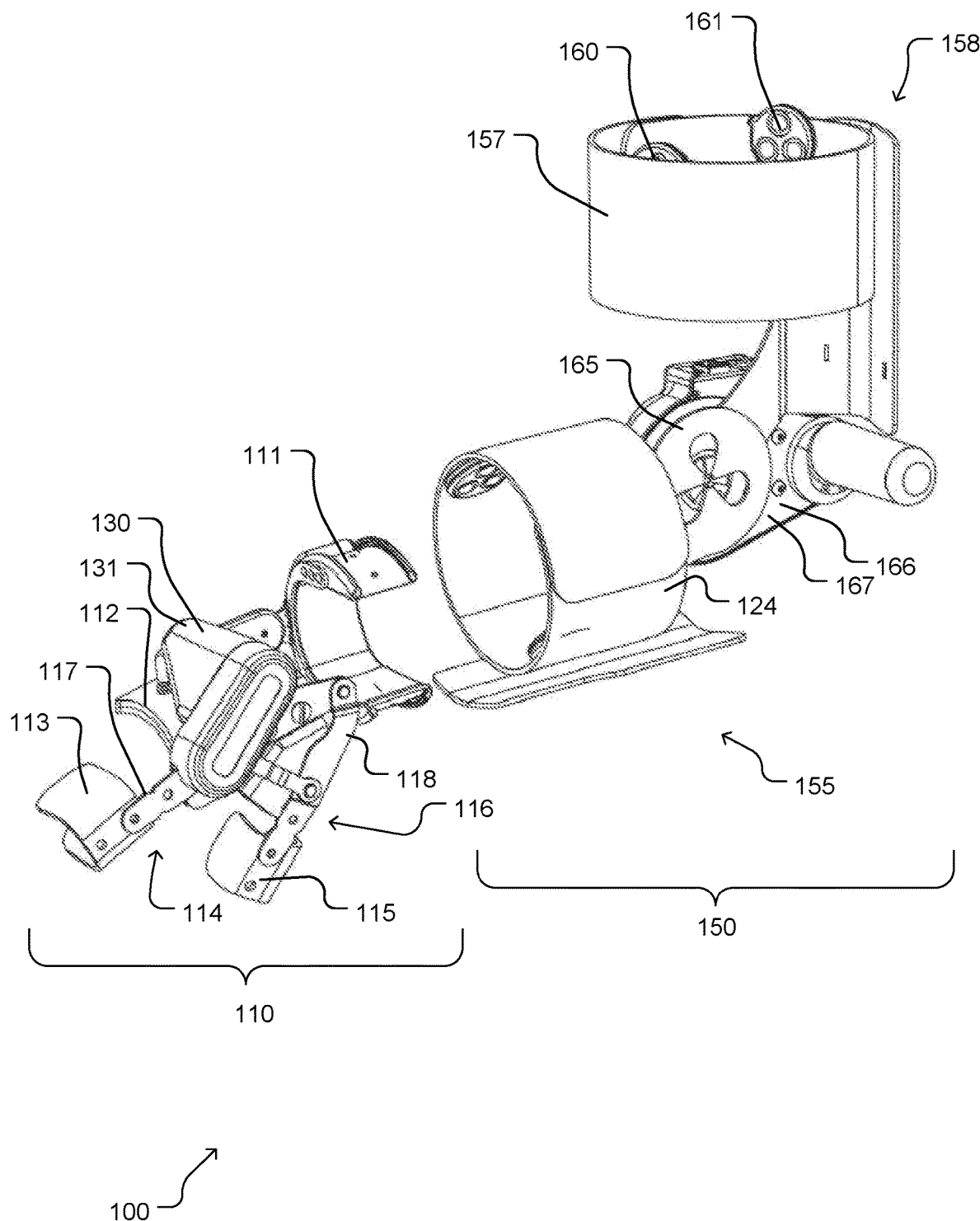
FIG. 4 shows the powered orthotic device of FIG. 3, as detached from the limb.

FIGS. 1 and 3 show isometric views of a powered orthotic device 100 including a brace system with two brace sub-assemblies 110, 150 that are removably attached to a limb of a subject, and FIGS. 2 and 4 show the device 100, from the respective views, as detached from the limb. Both brace sub-assemblies 110, 150 may be wearable components that are configured to be removably attached to limb segments of a user.

In this embodiment, the second brace sub-assembly 110 of the device 100 is configured to be coupled to the hand and forearm of a user. To removably attach the second brace sub-assembly 110 to the user, the user inserts a wrist into the cuff 111 and positions the back of his or her hand under a molding 112 that supports an actuator assembly 130. The user also inserts one or more fingers into a splint 113 of a first section 114 of the second brace sub-assembly 110, as well as a thumb into a splint 115 of a second section 116. In some embodiments, a strap 124 may be attached to the second brace sub-assembly 110, and to further secure the second brace sub-assembly 110 to the user's limb, the user may wrap the strap 124 around his or her forearm, and clasp the ends of the strap 124 together. In this embodiment, in which two EMG sensors 120, 121 are affixed to the strap 124, attaching the second brace sub-assembly 110 to the user couples the EMG sensors 120, 121 to at least one muscle group in the user's forearm.

The actuator assembly 130 includes a processor, and a motor and drive assembly coupled to the first and section sections 114, 116. The actuator assembly 130 receives output from the EMG sensors 120, 121, and based on at least these signals, the actuator assembly 130 determines the torque to apply to the first and second sections 114, 116 of the second brace sub-assembly 110 so that the sections 114, 116 move relative to one another. The processor outputs a signal to the motor and drive assembly to move the sections 114, 116 accordingly.

For example, one side of the actuator assembly 130 may connect to a beam 117 attached to the splint 113 of the first section 114, and the other side may connect to a hinge 118 attached to the splint 115 of the second section 116. By driving the beam 117, the hinge 118, or both, by extension, the actuator assembly 130 drives the first and/or second sections 114, 116 to move relative to one another. Since the splints 113, 115 engage the user's finger(s) and thumb, the actuator assembly 130 supplements the user's control over these digits to achieve fine motion via, for example, radial and ulnar deviation.

The first brace sub-assembly 150 of the device 100 is configured to be coupled to the forearm and upper arm of a user. To attach the first brace sub-assembly 150 to the user's limb, the user may wrap a strap 157 attached to the first section 158 of the first brace sub-assembly 150 around the user's upper arm to secure the first section 158 to the user's limb. In some embodiments, the user may place his or her forearm into a curved recess of the second section 155 of the first brace sub-assembly 150. In further embodiments, a strap 124 is attached to the second section 155 of the first brace sub-assembly 150, and the user may further secure the first brace sub-assembly 150 to the user's forearm by wrapping the strap 124 around his or her forearm and clasping the ends of the strap 124 together. In various embodiments, the second section 155 may include one or more additional straps to wrap around the user's forearm.

As with the second brace sub-assembly 110, the strap 157 for the first brace sub-assembly 150 includes one or more EMG sensors 160, 161. When the user wraps the strap 157 around his or her upper arm, the EMG sensors 160, 161 become coupled to at least one muscle group in the user's upper arm. Further, the first brace sub-assembly 150 includes a powered actuator assembly 165 inside a housing 166. The actuator assembly includes a processor (not shown), and receives output from the one or more EMG sensors 160, 161. Based on at least these signals, the actuator assembly 165 drives the first and second sections 158, 155 of the first brace sub-assembly 150 to move relative to one another. By controlling the flexion and extension between the user's forearm and upper arm, the actuator assembly supplements the user's control over these limb segments to achieve gross motion for the limb.

The first brace sub-assembly 150 includes a user interface 170 on the housing 166 through which a user interacts with the device 100. In this embodiment, the user interface 170 includes a power button for turning the device on and off and a mode button for selecting the device's 100 mode of operation. In various embodiments, the user interface 170 may include other inputs for user input and feedback, such as single or multiple knobs, buttons, switches, touch sensors, touch screens, or combinations thereof. The user interface 170 may include outputs, such as audio and/or visual devices, e.g., speakers, lights, LEDs, tactile sensors or transmitters, visual displays, such as LCD screens. Additionally, the first brace sub-assembly 150 may include a data storage and management system (not shown) within the same housing 166 that covers the actuator assembly 165.

Figure 5:
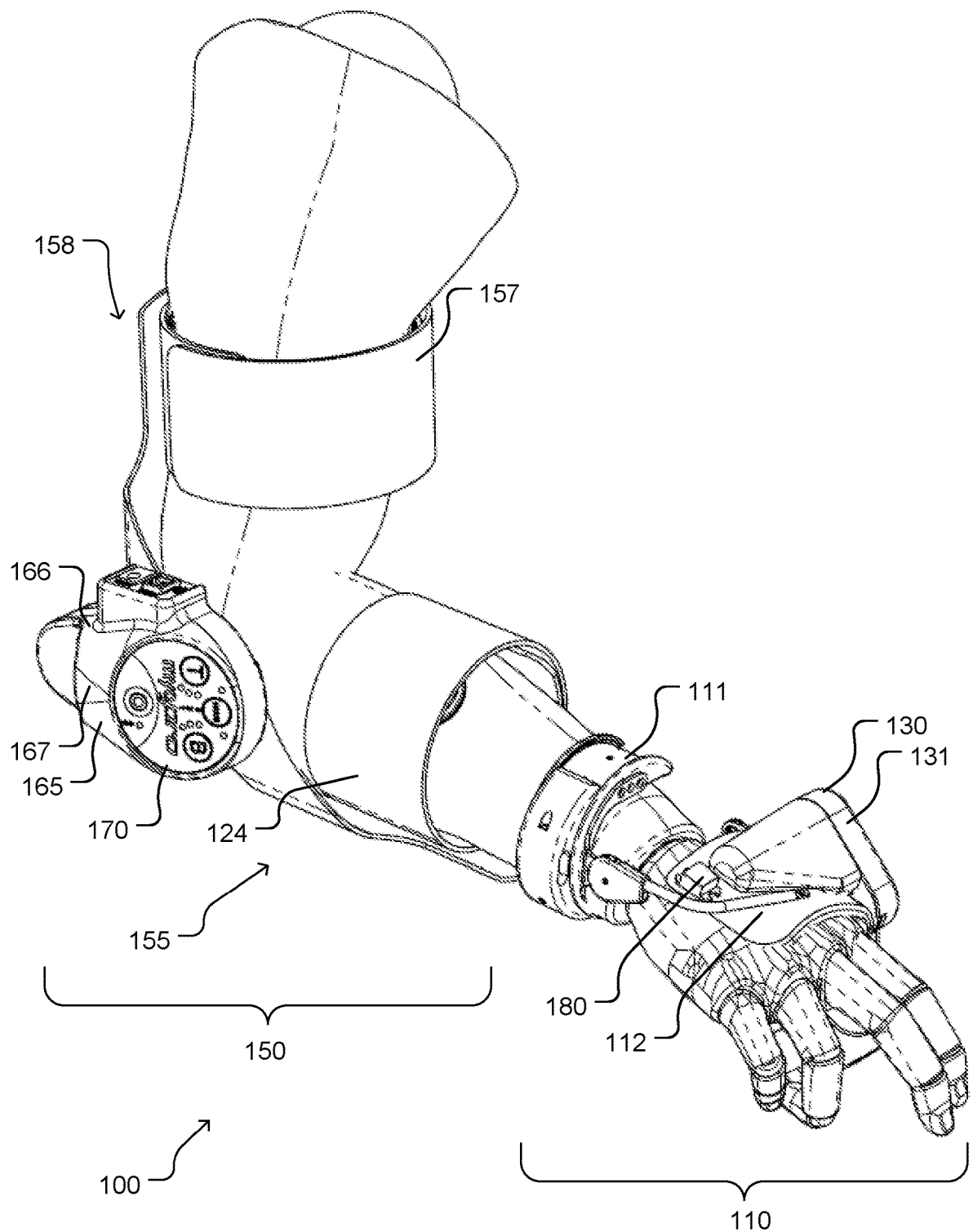
FIGS. 5-7 show isometric views of a powered orthotic device including a brace system with two brace sub-assemblies that are removably attached to a limb of a subject, wherein the second brace sub-assembly further includes an inertial measurement unit.
Figure 6:
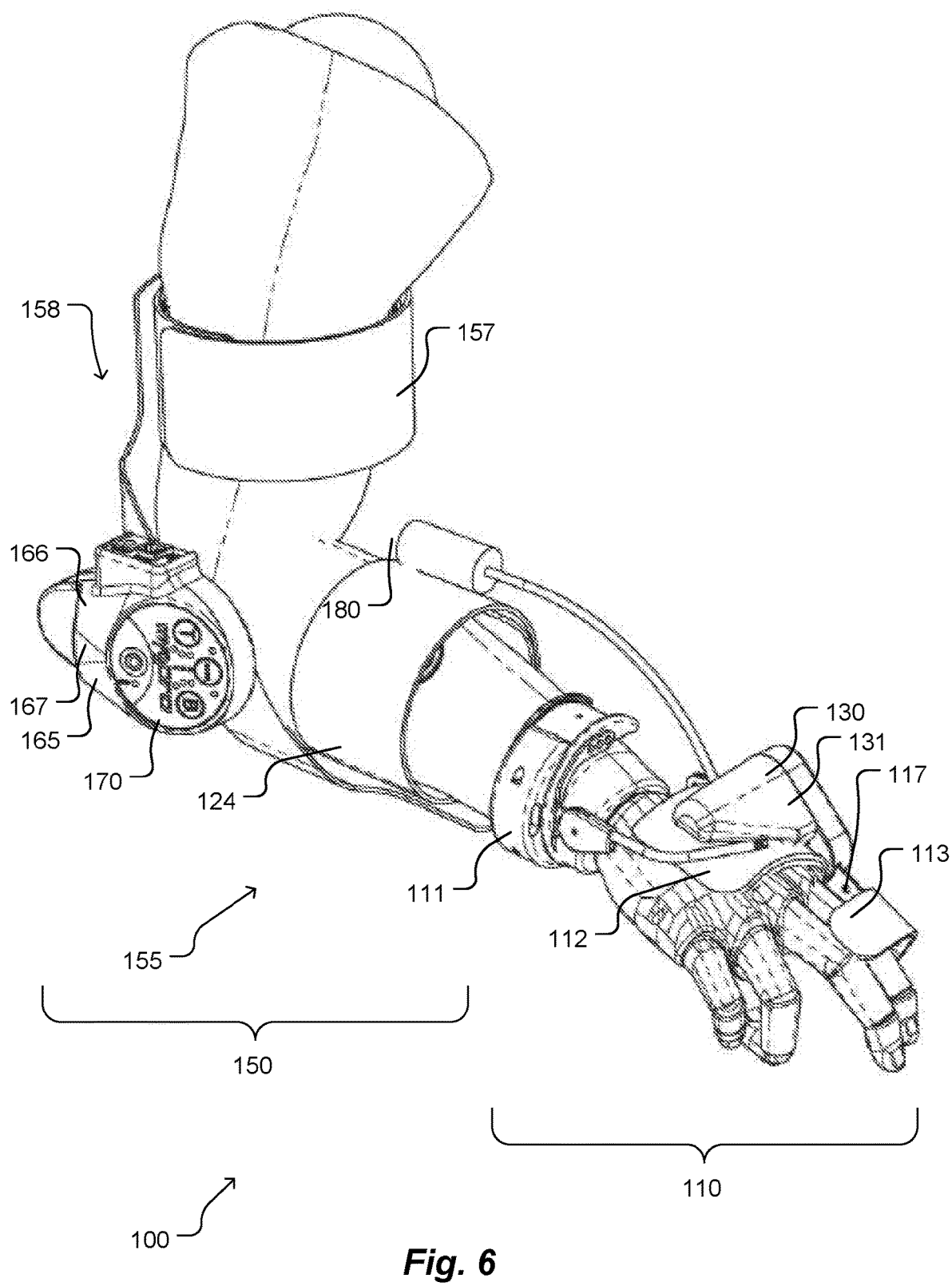
Figure 7:
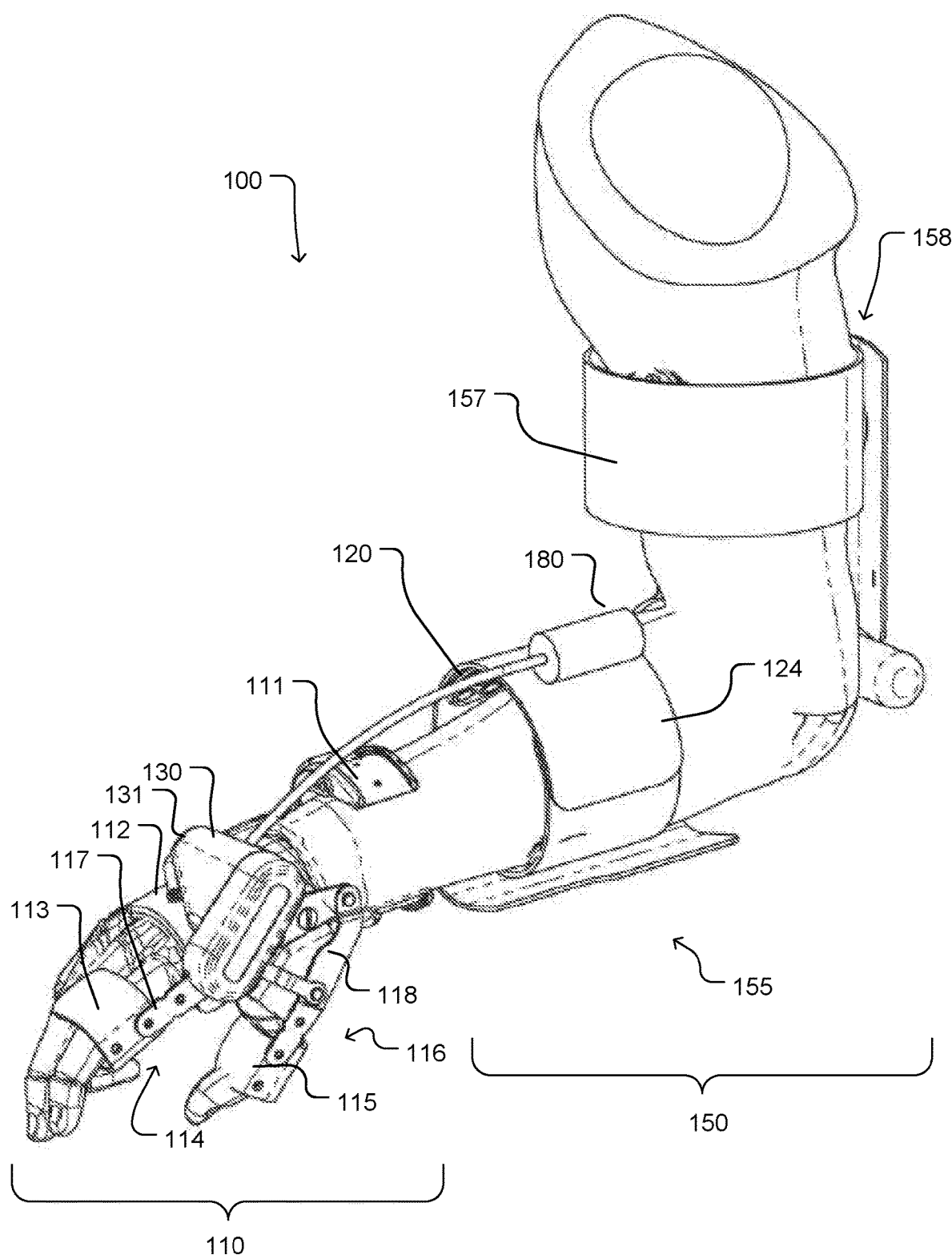

In various embodiments, the housing 166 on the first brace sub-assembly 150 may include a controller system 167 that interacts with the actuator assemblies 130, 165 of the first and second brace sub-assemblies 150, 110. In some embodiments, each brace sub-assembly 150, 110 includes a processor that receives outputs from its respective EMG sensors 160, 161, or 120, 121, processes the outputs according to control algorithms, and drives its respective actuator assembly 165 or 130 accordingly. However, in further embodiments, the EMG sensors 120, 121, 160, and 161 may all send their outputs to the controller system 167. Based on these outputs, the processing system in the controller system 167 may determine the torques to apply to the first and second sections of each brace sub-assembly 150, 110. Moreover, in some embodiments, the processing system may determine the torque to apply to the second brace sub-assembly 110 based on signals from EMG sensors 160, 161 in the first brace sub-assembly 150, as well as the EMG sensors 120, 121 and/or one or more inertial measurement units 180 (as described in more detail below in FIGS. 5-7) in its own second brace sub-assembly 110. Likewise, the processing system may determine the torque to apply to the first brace sub-assembly 150 based on signals from EMG sensors 160, and 161 as well as the EMG sensors 120, 121 and/or the inertial measurement units 180 in both the first and second brace sub-assemblies 150, 110.

Turning now to FIGS. 5-9, the figures show isometric views of a powered orthotic device 100 that includes the features described with respect to FIGS. 1-4, and also includes at least one inertial measurement unit (IMU) 180. In the embodiment depicted in FIG. 5, the IMU 180 is attached to the molding 12 of the second brace sub-assembly 110 and is thus configured to be coupled to a user's hand. The IMU 180 may send its output to the actuator assembly 130 of the second brace sub-assembly 110. In the embodiments depicted in FIGS. 6 and 7, the IMU 180 is attached to the strap 124 configured to be wrapped around the user's forearm, and the IMU 180 may send its output to the actuator assembly 130 of the second brace sub-assembly 110. In any of these embodiments, the actuator assembly 130 determines the torque for driving the first and second sections 114, 116 based solely on the output of the IMU 180, and in other, additional embodiments, the actuator assembly 130 determines the torque based on outputs from both the IMU 180 and the EMG sensors 120, 121 of the strap 124.

Figure 8:
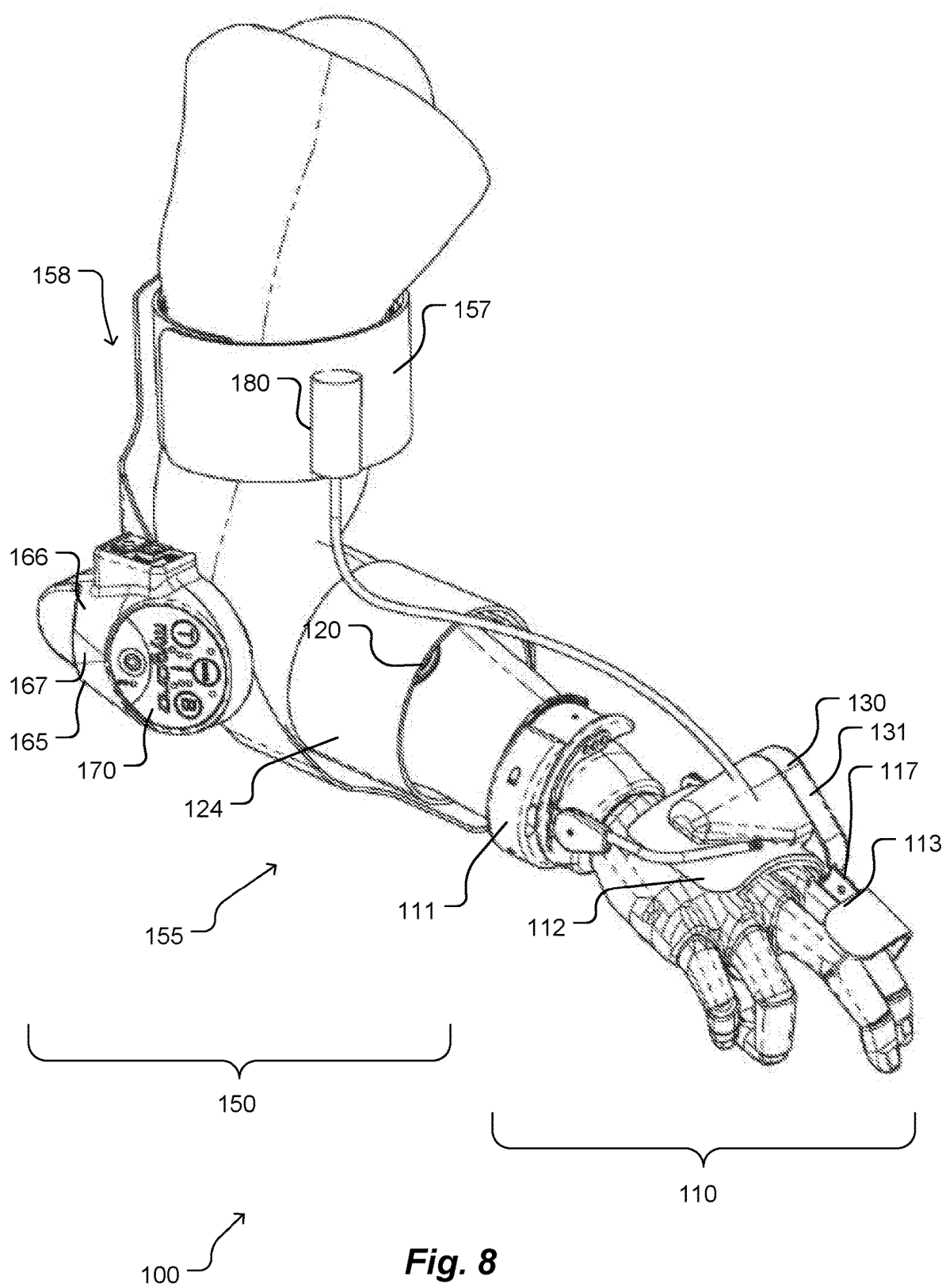
FIGS. 8 and 9 show isometric views of a powered orthotic device including a brace system with two brace sub-assemblies that are removably attached to a limb of a subject, wherein the first brace sub-assembly further includes an inertial measurement unit.
Figure 9:
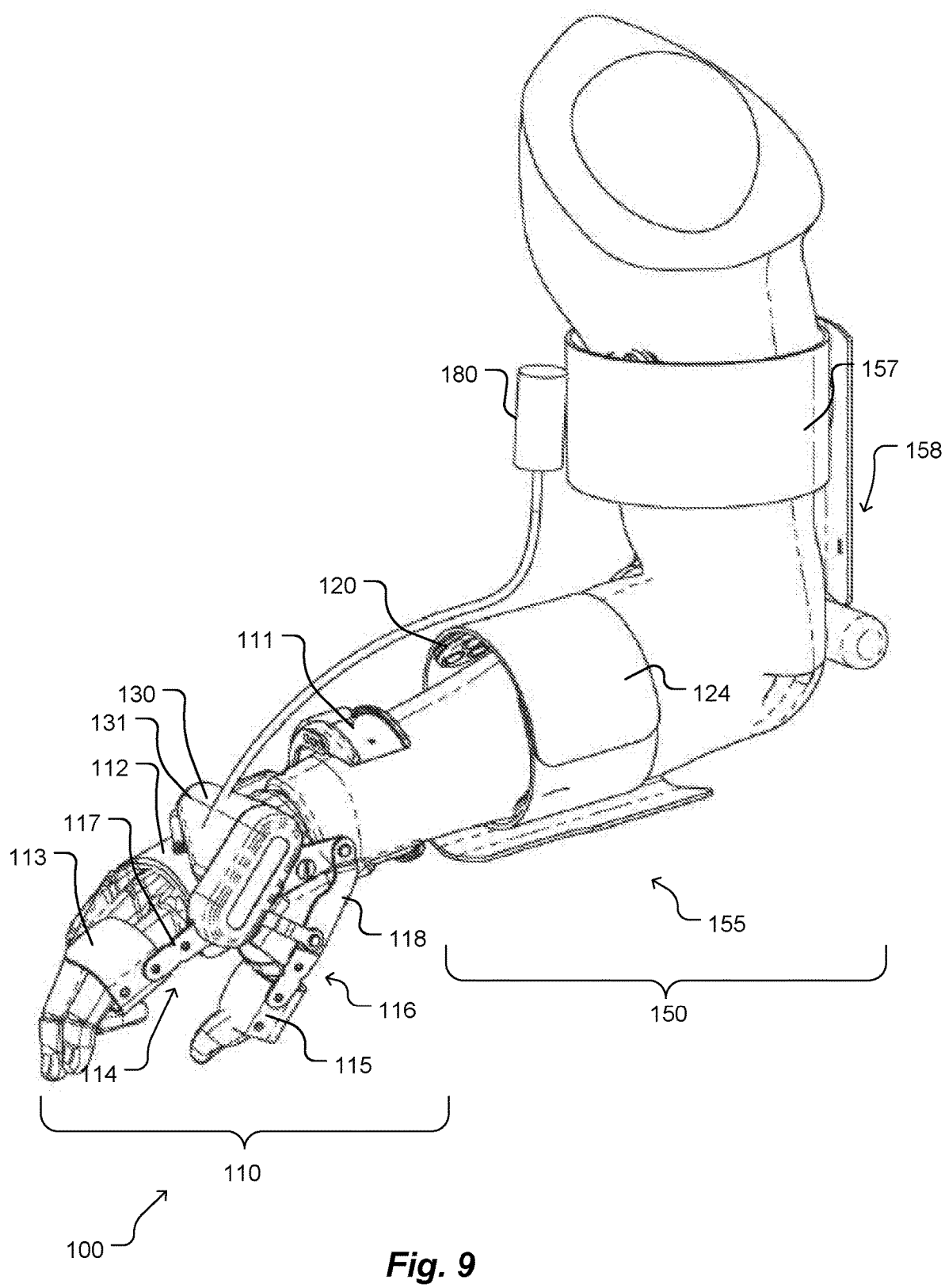

In the embodiments depicted in FIGS. 8 and 9, the IMU 180 attaches to the strap 157 of the first brace sub-assembly 150, and the strap 157 is configured to be wrapped around the user's upper arm. In this embodiment, the output of the IMU 180 is still used to drive the second brace sub-assembly 110. In particular, the IMU 180 may send its output to the actuator assembly 130 in the housing 131 of the second brace sub-assembly 110. As with the embodiments of FIGS. 5-7, the actuator assembly 130 may determine the torque for driving the first and second sections 114, 116 based solely on the output of the IMU 180 or a combination of outputs from the IMU 180 and EMG sensors 120, 121 attached to the strap 124.

Figure 10:
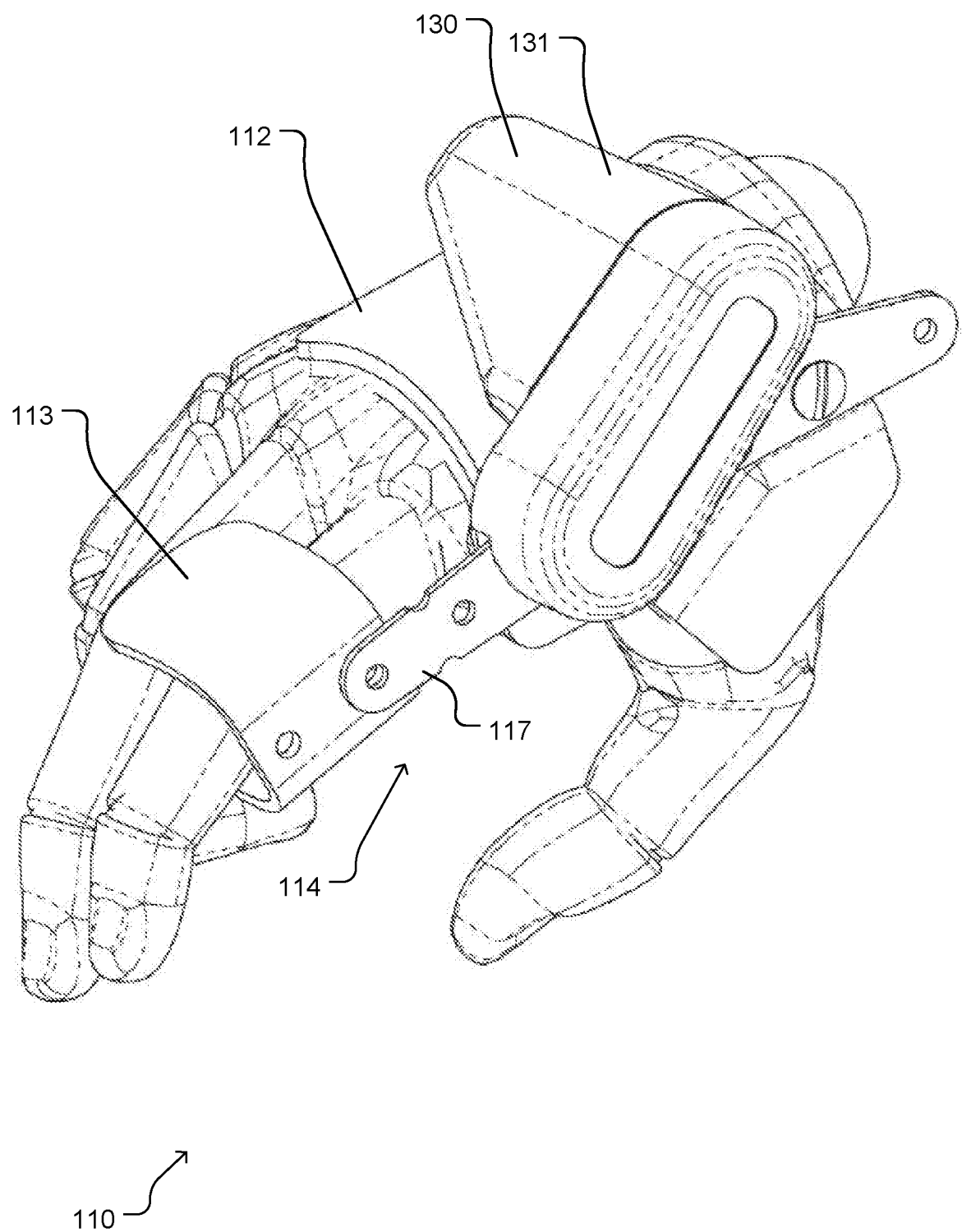
FIG. 10 shows an isometric view of part of a second brace sub-assembly of a powered orthotic device, with the first section of the second brace sub-assembly removably attached to a limb segment.

Turning now to FIG. 10, the figure shows an isometric view of part of the second brace sub-assembly 110 of a powered orthotic device 100. This figure depicts the molding 112, the actuator assembly 130, and the first section 114 of the second brace sub-assembly 110. As this embodiment drives the first section 114 to move, the embodiment may be used for persons who have diminished control over the joints in their index and second fingers, but who retain control over the joints in their thumbs.

Further, this embodiment includes an adjustable splint 113. Both the splint 113 and the beam 117 may include two or more holes, and a user may align different holes in the splint 113 and the beam 117 to position the splint 113 on the user's fingers. The user may secure the splint 113 by inserting a screw or other fastener into the aligned holes, although other mechanisms of securing the components may be used.

By changing the position of the splint 113 on the user's fingers, the second brace sub-assembly 110 may create different ranges of motion for the user. Moreover, by allowing the splint 113 to be detached, the user 113 may apply different splints 113 to the second brace sub-assembly 110, as desired. For example, the user may select a splint 113 whose size matches the user's own fingers. Additionally, the user may choose a splint 113 that engages either the user's index finger alone, or the user's index finger with one or more additional fingers.

Figure 11:
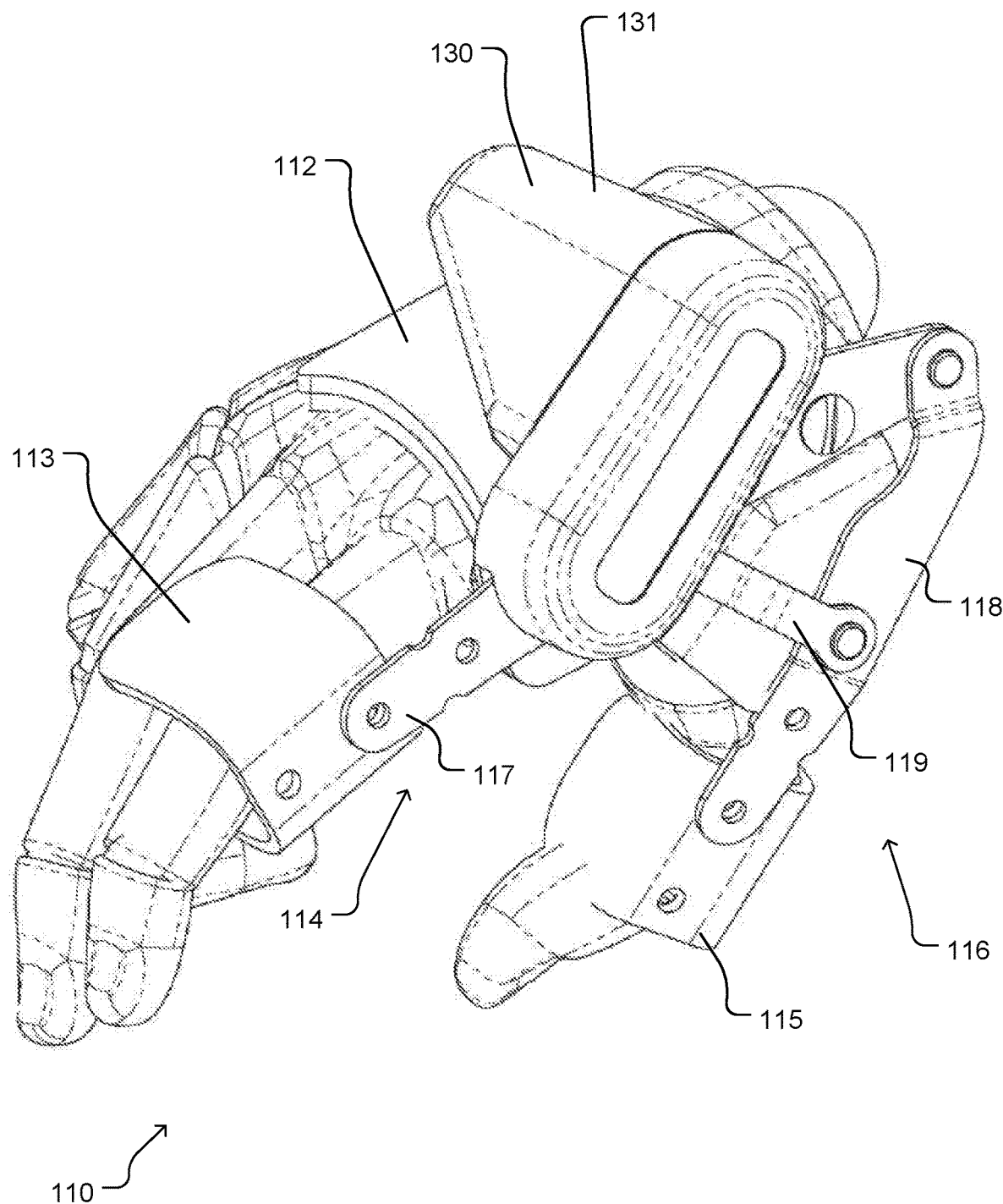
FIG. 11 shows an isometric view of a second brace sub-assembly of a powered orthotic device, with the first and second sections of the second brace sub-assembly removably attached to corresponding limb segments.
Figure 12:
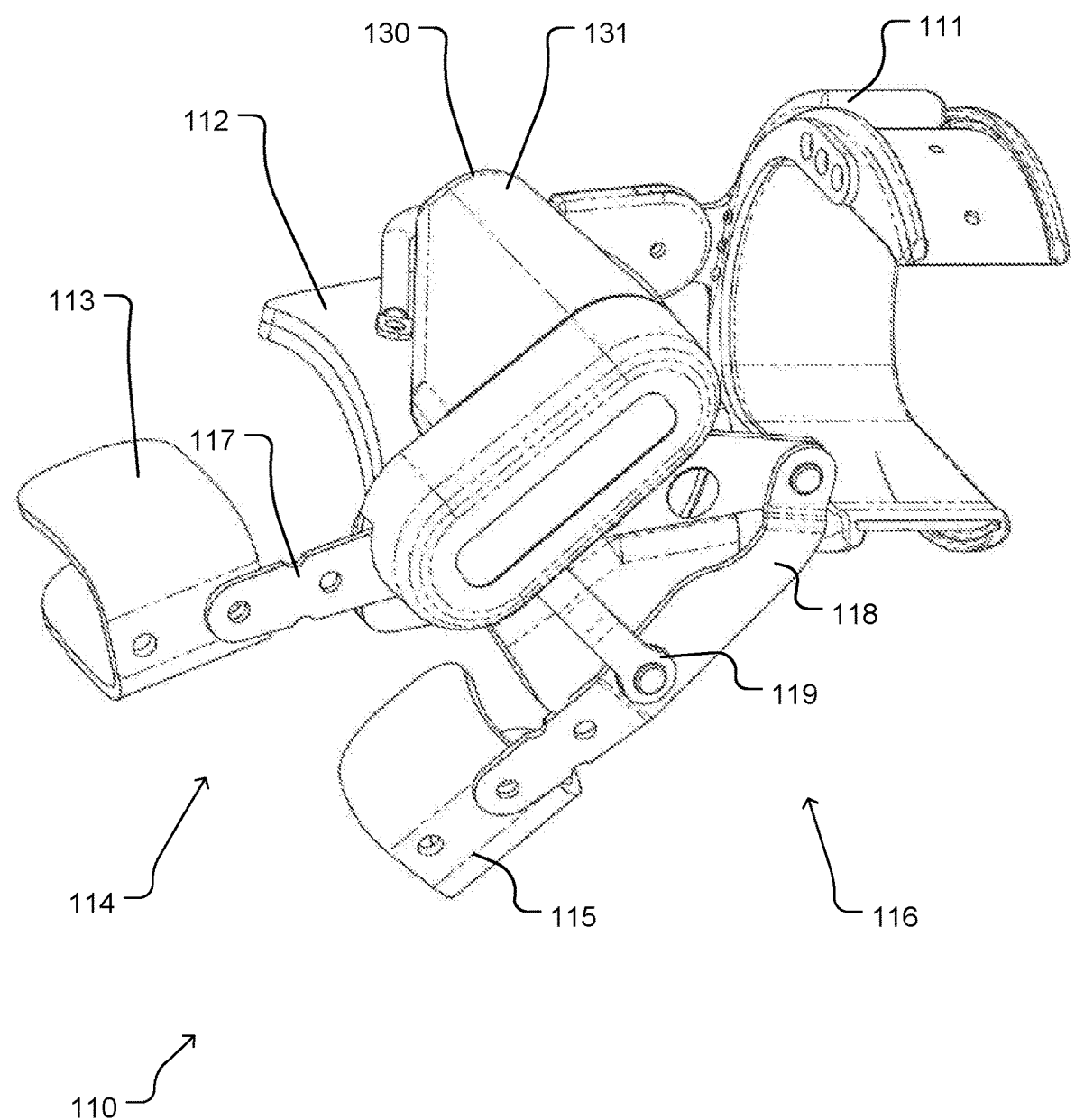
FIG. 12 shows an isometric view of a second brace sub-assembly, as detached from any limbs.

FIG. 11 shows an isometric view of the second brace sub-assembly 110 with both the first and second sections 114, 116 (FIG. 12 depicts a second brace sub-assembly 110 that includes the features of the second brace sub-assembly 110 of FIG. 11, as well as a cuff 111, but detached from the user's hand). This second brace sub-assembly 110 includes the components of the first section 114 described in reference to FIG. 10. Moreover, this figure depicts a splint 115 configured to engage a user's thumb, as well as a hinge 118 attached to the splint 115. The hinge 118 is also attached to the actuator assembly 130, which drives the hinge 118 to move the user's thumb via the second section 116. As with the first section 114, the splint 115 and the hinge 118 may include multiple holes for aligning the former on the latter at different positions, or for changing splints 115 according to the needs of the user.

The second section 116 may also include a beam 119 attached to the actuator assembly 130 and the hinge 118. Although the actuator assembly 130 does not drive the beam 119, the positions where the beam 119 attaches to the actuator assembly 130 and the hinge 118 enable the beam 119 to modify the movement of the hinge 118, and thus, the position of the splint 115. Further, the beam 119 may be adjustably attached to different positions on the hinge 118, and from each position, the beam 119 may modify the movement of the hinge 118 and splint 115 in a different manner. As a result, the second brace sub-assembly 110 may be configured to mimic different natural motions of the hand, depending on the setting of the beam 119. In this embodiment, the hinge 118 includes three notches to which the beam 119 may be attached. The beam 119 may have a hole at one end, and the user may align the hole with one of the notches and insert a screw to secure the beam 119 to the hinge 118. However, other embodiments of the beam 119 and hinge 118 may use alternate means of fastening (e.g., the beam 119 may include a hook to insert into a notch).

Although the actuator assembly 130 may drive the hinge 118 and not the beam 119, in various embodiments, the actuator assembly 130 may drive solely the beam 119. Alternatively, the actuator assembly 130 may drive both the hinge 118 and the beam 119.

Figure 13:
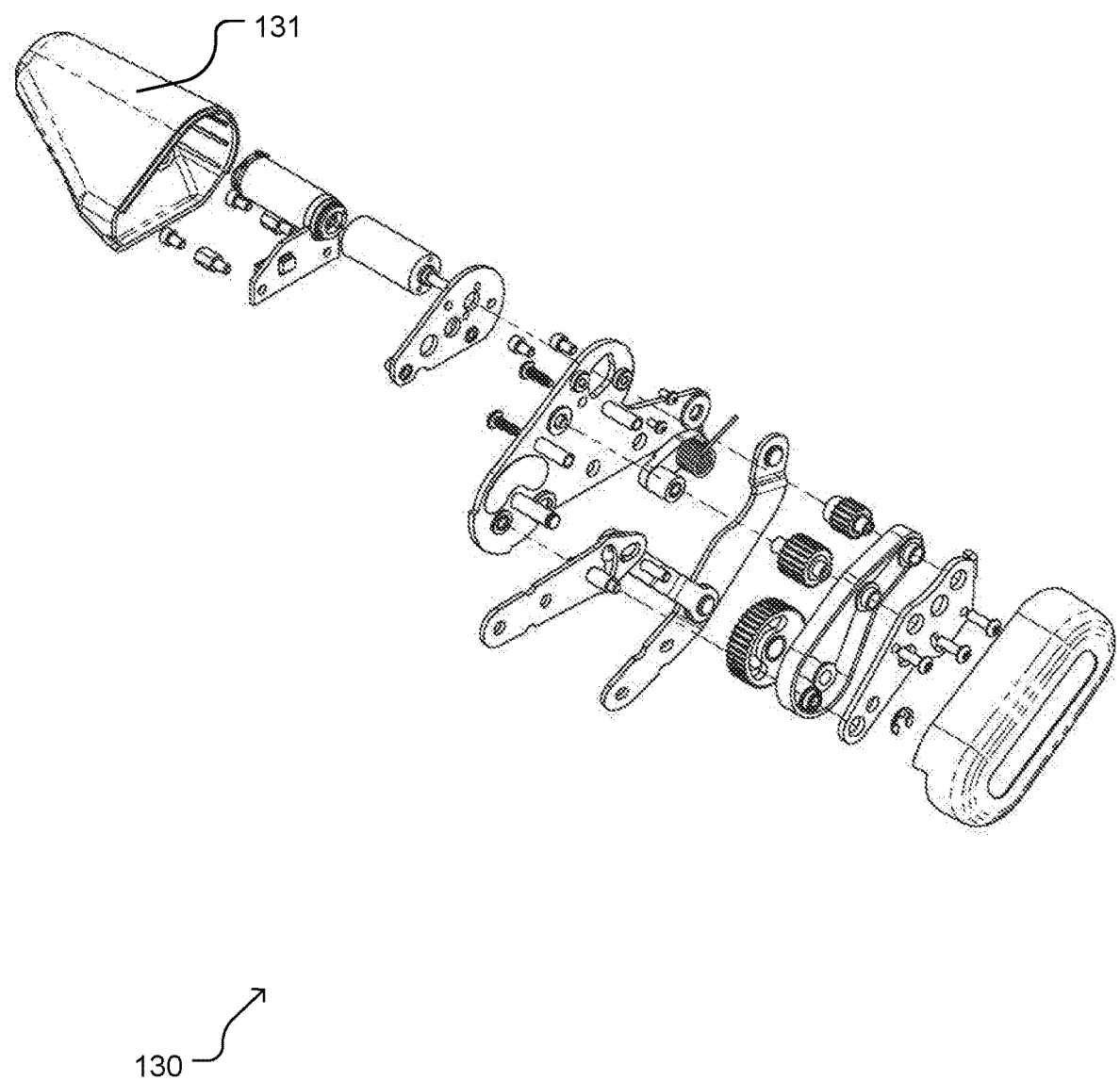
FIGS. 13-15 show exploded views of the actuator assembly of the second brace sub-assembly.
Figure 14:
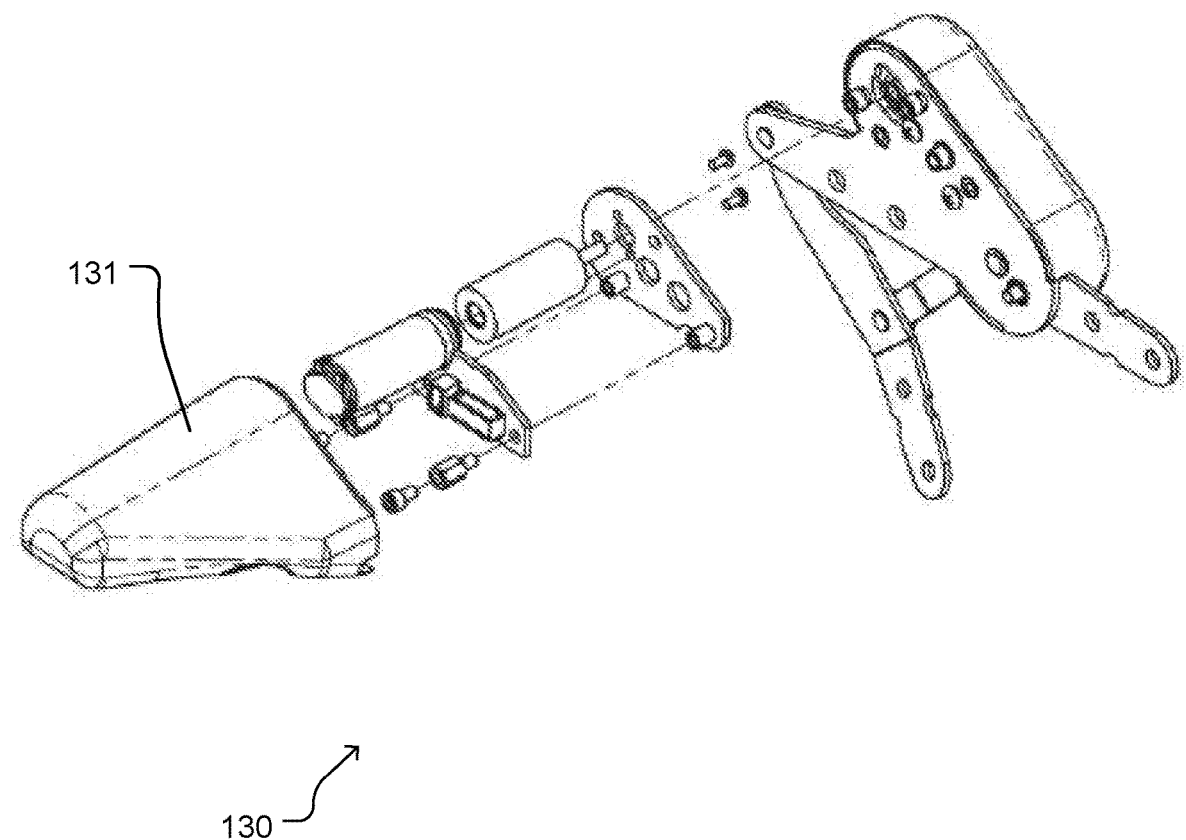
Figure 15:
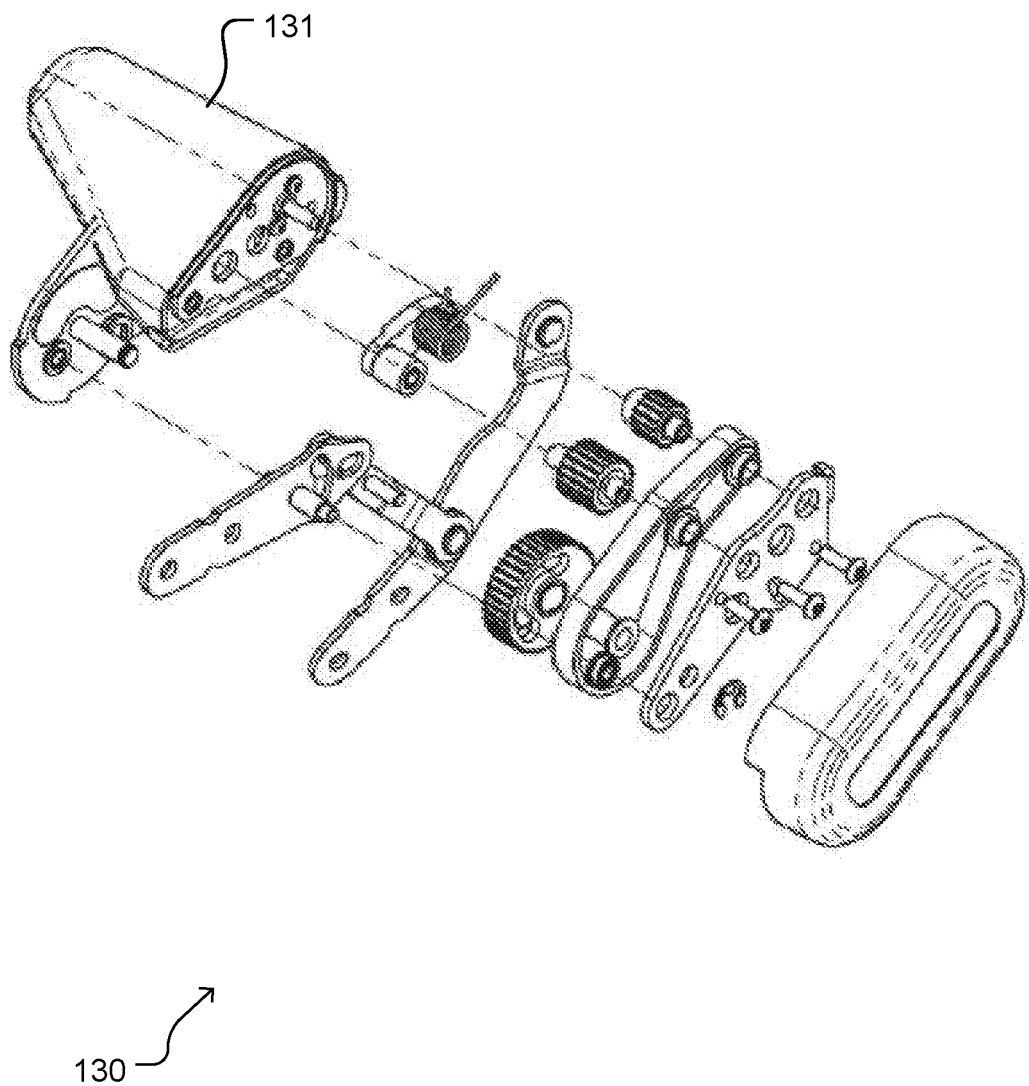

FIGS. 13-15 show exploded views of the actuator assembly 130 of the second brace sub-assembly 110. FIG. 13 depicts the entire actuator assembly 130, FIG. 14 depicts components of the assembly 130 positioned on one side of the hinge 118, and FIG. 15 depicts components of the assembly 130 positioned on the opposite side of the hinge 118.

Figure 16:
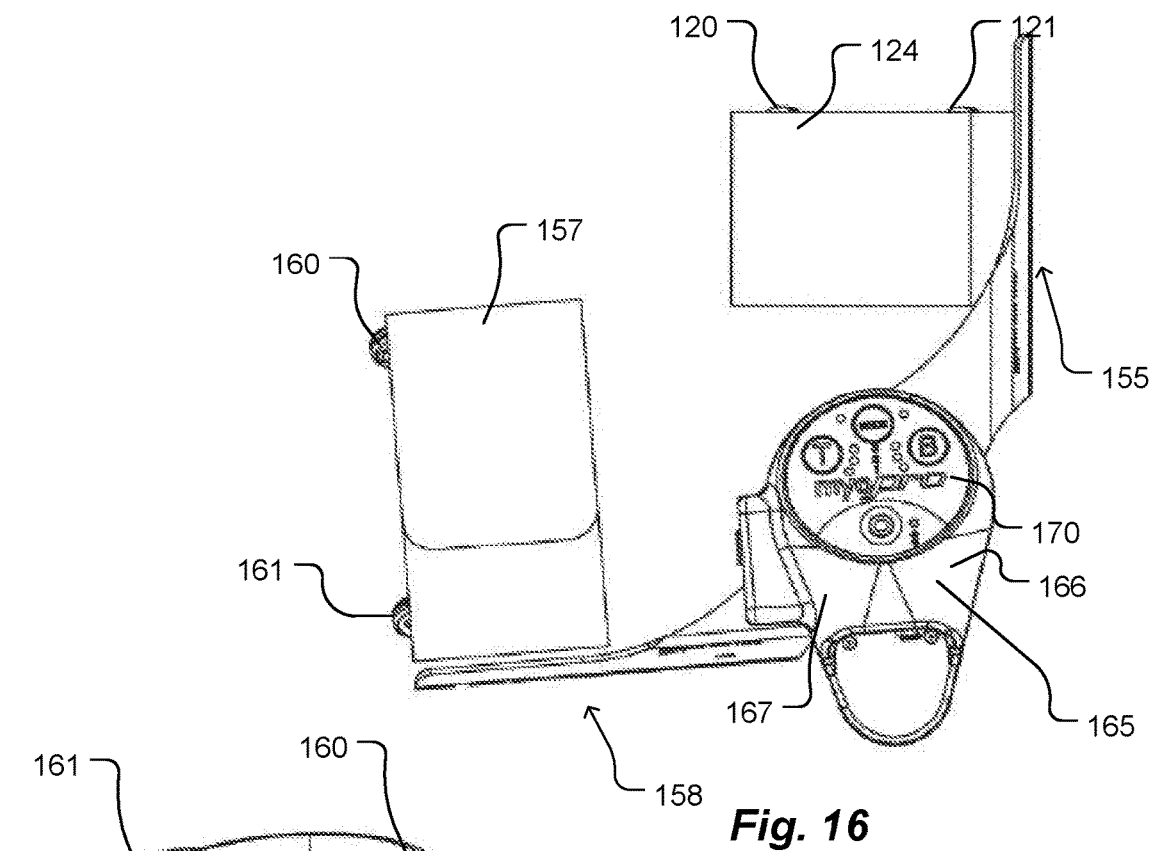
FIGS. 16 and 17 show elevation and isometric views, respectively, of the first brace sub-assembly.
Figure 17:
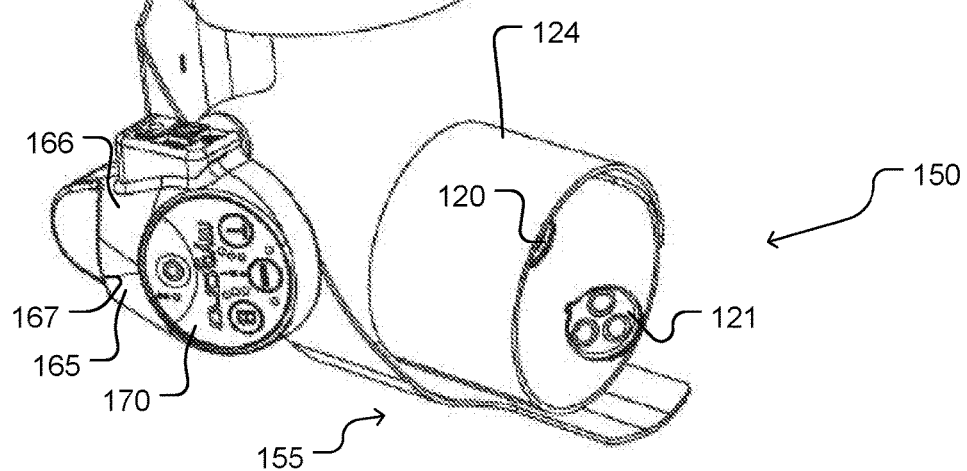

FIGS. 16 and 17 show elevation and isometric views, respectively, of the first brace sub-assembly 150. The first brace sub-assembly 150 includes the first and second sections 158, 155 and the actuator assembly 165 that drives the sections 158, 155 to move relative to one another. The first brace sub-assembly 150 also includes the strap 157 for removably attaching the first brace sub-assembly 150 to the user's upper arm. In this embodiment, the strap 124 with EMG sensors 120, 121 that send their outputs to the second brace sub-assembly 110 is attached to the second section 155 of the first brace sub-assembly 150. Thus, the user may use straps 124 and 157 to secure the first brace sub-assembly 150 to the user's forearm and upper arm, while the second brace sub-assembly 110 may be removably attached to the user's limb via the cuff 111.

Figure 18:
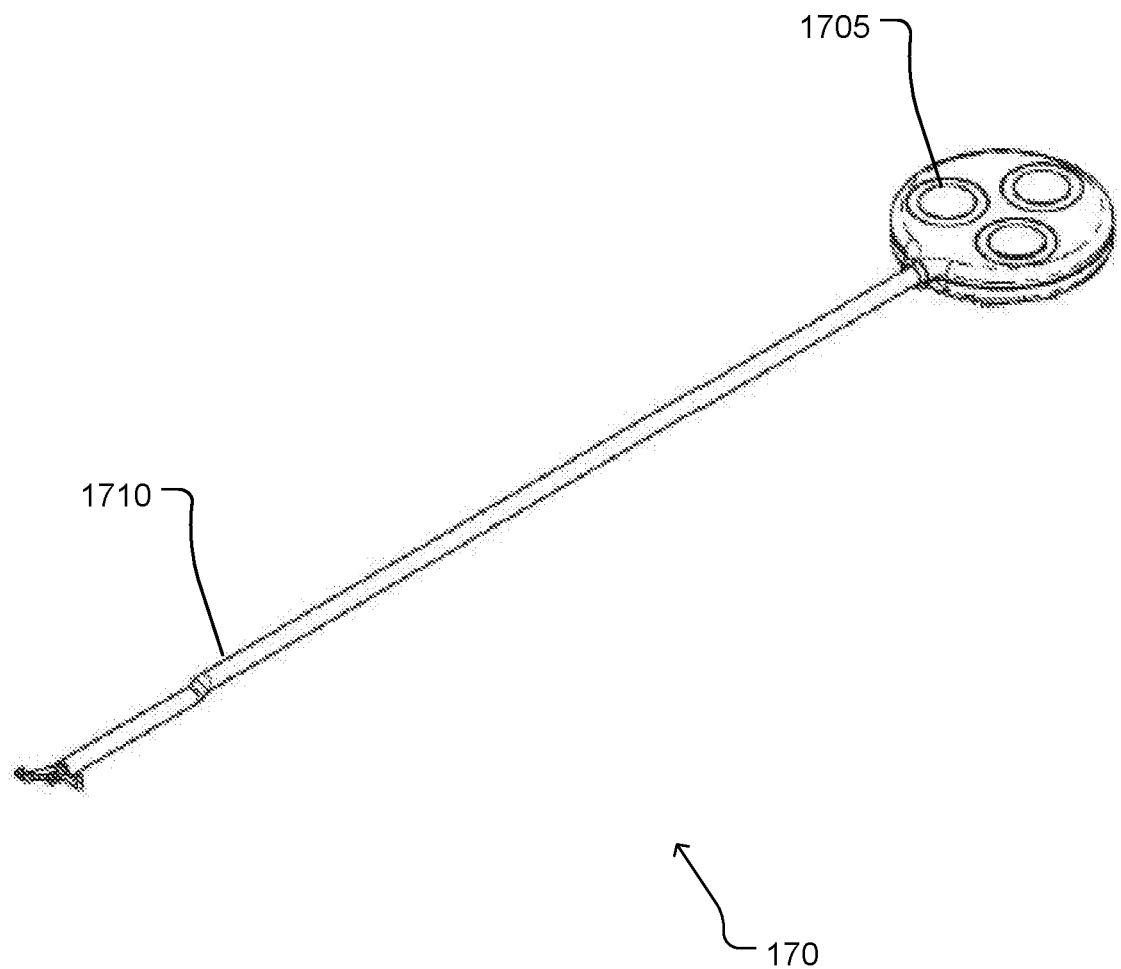
FIG. 18 shows an exemplary electromyographic sensor for use with the first and second brace sub-assemblies.

FIG. 18 shows an exemplary electromyographic (EMG) sensor 1701 for use with the first and second brace sub-assemblies 150, 110. This EMG sensor includes a three-button array 1705, as well as a cable 1710 that receives output from the array 1705 and transmits the signals to another component.

Exemplary Embodiments of the Control Algorithm for Operating the Powered Orthotic Device FIGS. 19-29 show various exemplary control algorithms for driving the first or second brace sub-assemblies 150, 110. FIG. 19 shows an exemplary control algorithm and the variables upon which the algorithm is based that may be used in an orthotic device 100 in accordance with embodiments of the present invention. The control output signal is the command that is sent to the actuator assembly 130, 165. FIG. 19 depicts ways in which the various control output signal relationships may be combined to provide one command signal which commands the actuator assembly 130, 165. As shown, a simple arithmetic combination may be used (1'), in which the output signals from the various relationships (some of which are shown in FIGS. 21-27 below) are added, subtracted, multiplied, divided, or any combination (linear or non-linear (2')) thereof, to generate the command signal to the actuator assembly 130, 165. A conditional relationship may be used (3', 4'), in which the algorithm for combining the various output signals is dependent on certain conditions being met. Boolean combinations of such conditional relationships (4') may also be used. Also, any combination of the above mentioned techniques may also be used to combine the various output signals to generate one command signal.

Figure 20:
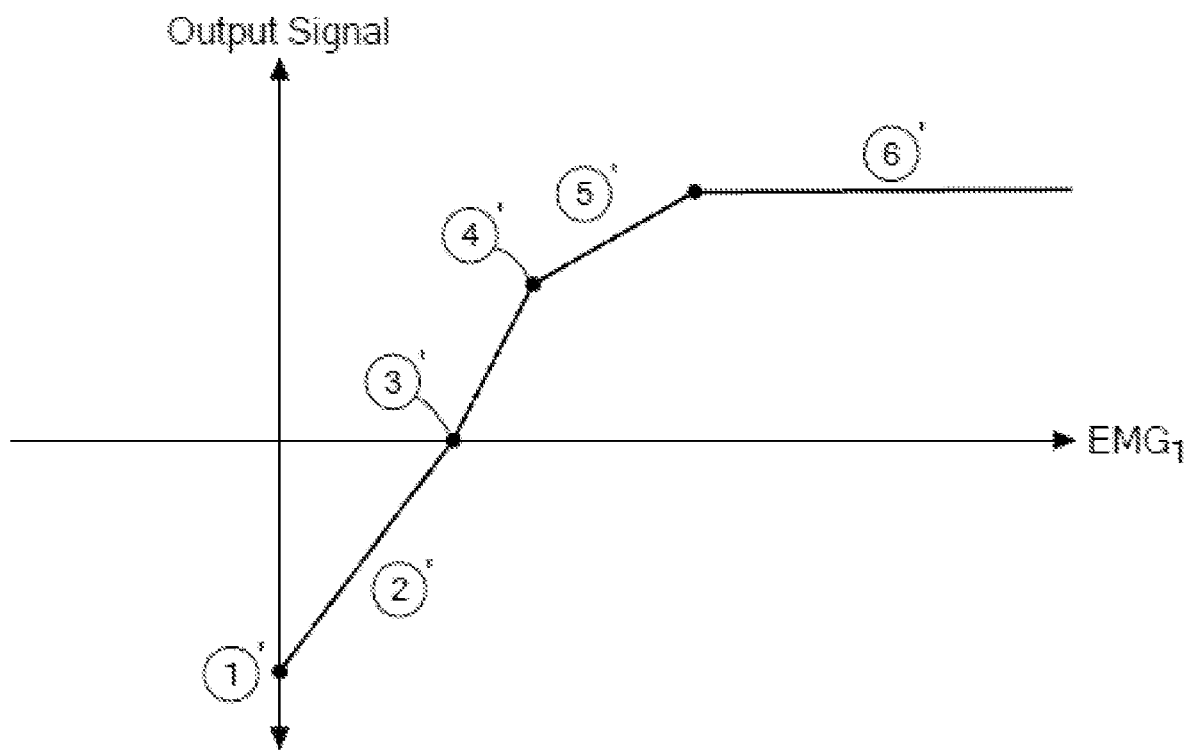
FIG. 20 shows a graph of EMG signal vs. output signal according to exemplary embodiments of the present invention.

FIG. 20 shows a graph depicting features of a control algorithm, namely the relationship between the control output signal and the measured EMG signal from a user's muscle (EMG1). In FIGS. 20-24, the axes have the following meaning: positive output signal correlates to actuator torque, velocity or motion in a first direction about the joint; negative output signal correlates to actuator torque, velocity or motion in a second direction about the joint; and EMG1 is the filtered absolute value of the EMG signal in the first direction. In FIG. 20, the y-intercept (1') is the maximum output signal in the second direction. This is the output signal that the system will give when the value of EMG1 is zero. The correlation between the output signal and EMG1 may be linear or non-linear, and may be considered in two separate regions: the first direction (4', 5', 6'), and the second direction (2'). The zero-crossing point (3') is the value of EMG1 at which the output signal changes direction. There may be break points (4') in any region, at which the slope of the relationship changes, or at which the relationship may change from linear to non-linear. There may be saturation limits (6') where the slope of the relationship goes to zero, meaning the output signal reaches a minimum or maximum "floor" or "ceiling" which it will not surpass, regardless of the value of EMG1. This may serve as a safety mechanism to prevent excessive torques in the case of abnormally high spikes in muscle activity.

Figure 21:
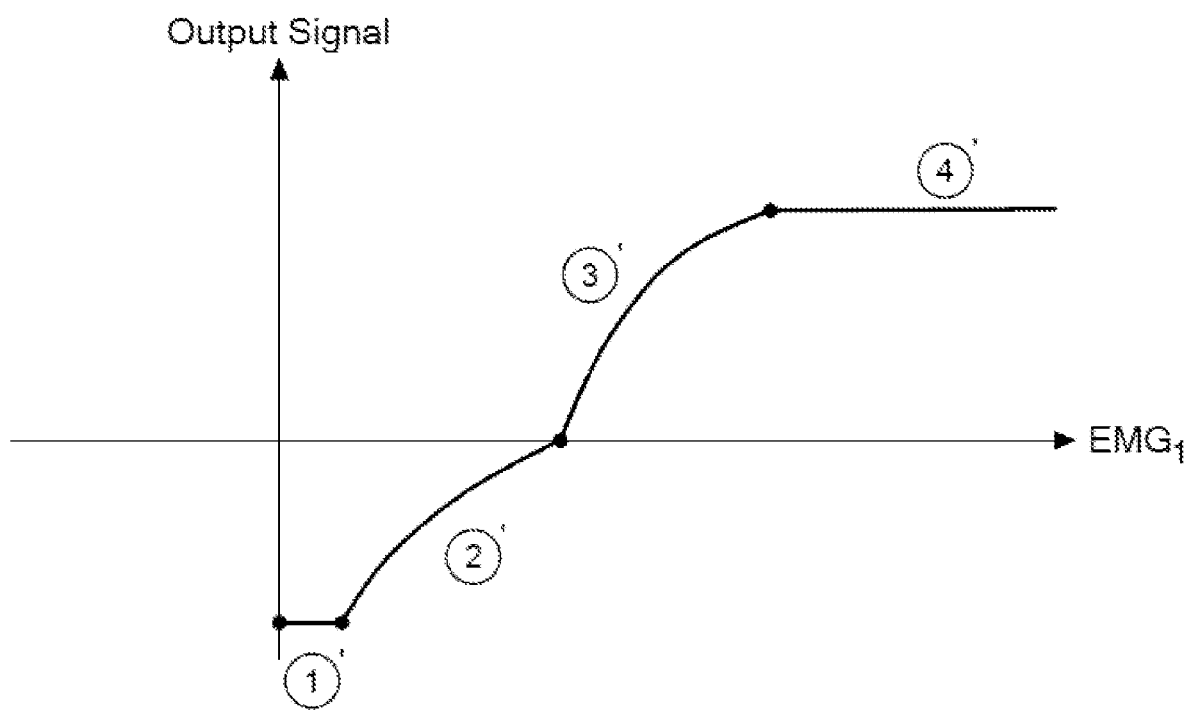
FIG. 21-24 show different graphs of EMG signal vs. output signal according to various exemplary embodiments of the present invention.

FIG. 21 shows a graph depicting features of another control algorithm. In this scenario, there may be output signal saturation in the second direction (1'), as well as in the first direction (4'). FIG. 21 also depicts a non-linear relationship between EMG1 and output signal in both the first (2') and second (3') directions, with a break point coinciding with the zero-crossing.

Figure 22:
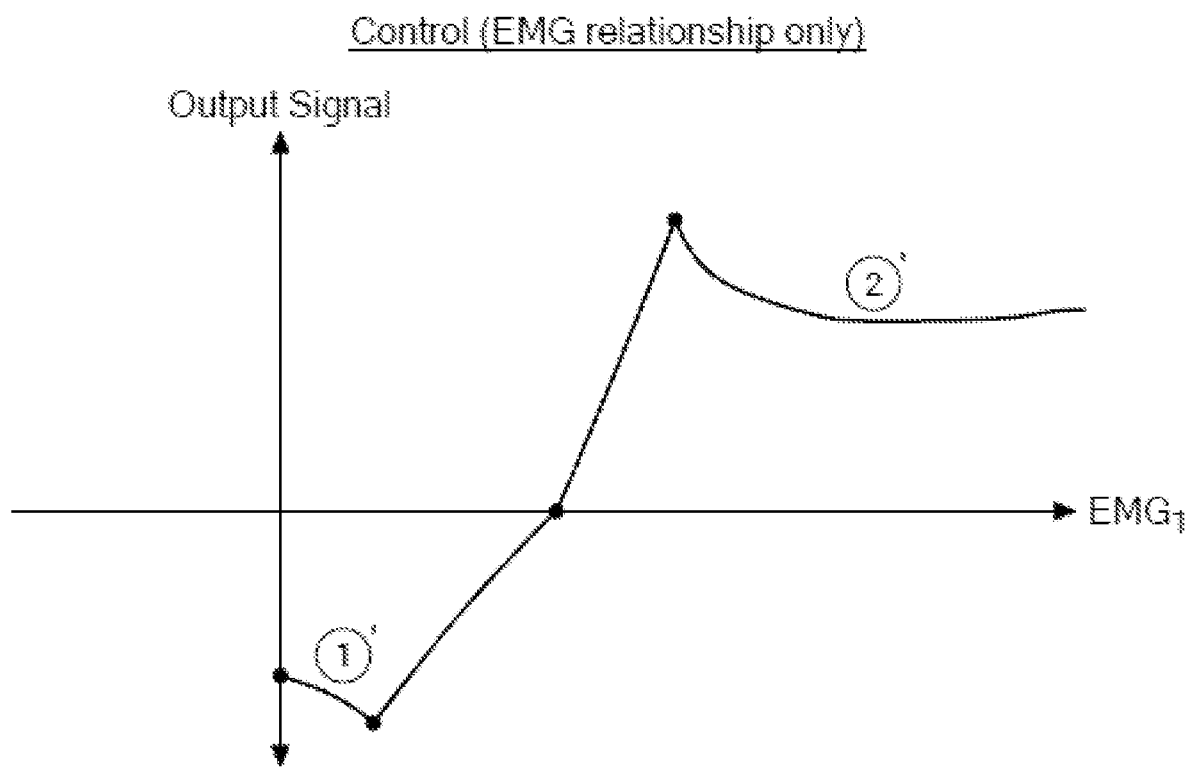

FIG. 22 shows a graph depicting features of another control algorithm. As shown, the relationship between output signal and EMG1 is not necessarily monotonic, but may have inflection points, where the slope changes from decreasing to increasing (1'), or vice versa (2'). For example, the maximum absolute output signal value for each direction may be reached before the output signal saturates, or before EMG1 reaches zero.

Figure 23:
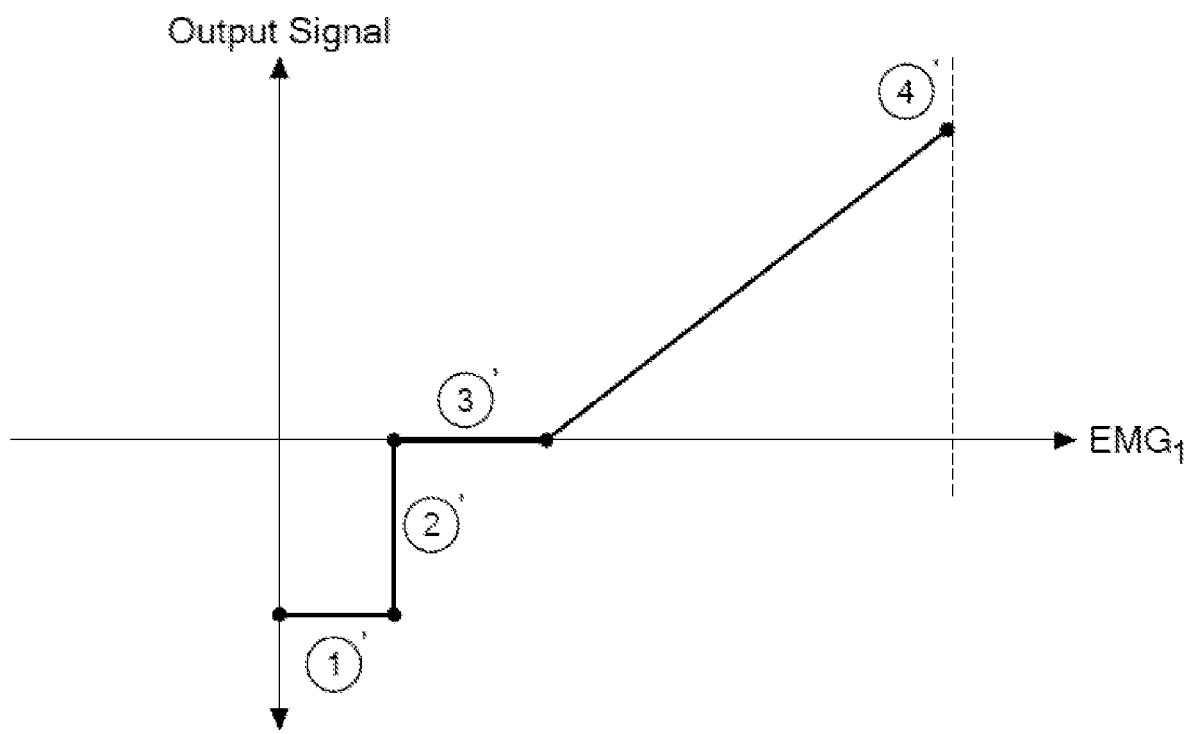

FIG. 23 shows a graph depicting features of another control algorithm. As shown, there may be regions of zero slope (1'), regions of infinite slope (2'), or discontinuities (3') in the relationship between output signal and EMG1. For example, the output signal may be constant for low values of EMG1 and then the value may jump to zero at a certain value of EMG1. Also, the output signal may not change direction (and cause torque in the first direction) until the value of EMG1 reaches yet another, higher value. This may be thought of as a "dead band" (3'), which may act to minimize the sensitivity of the output signal to small perturbations in EMG1 about some nominal value.

Figure 24:
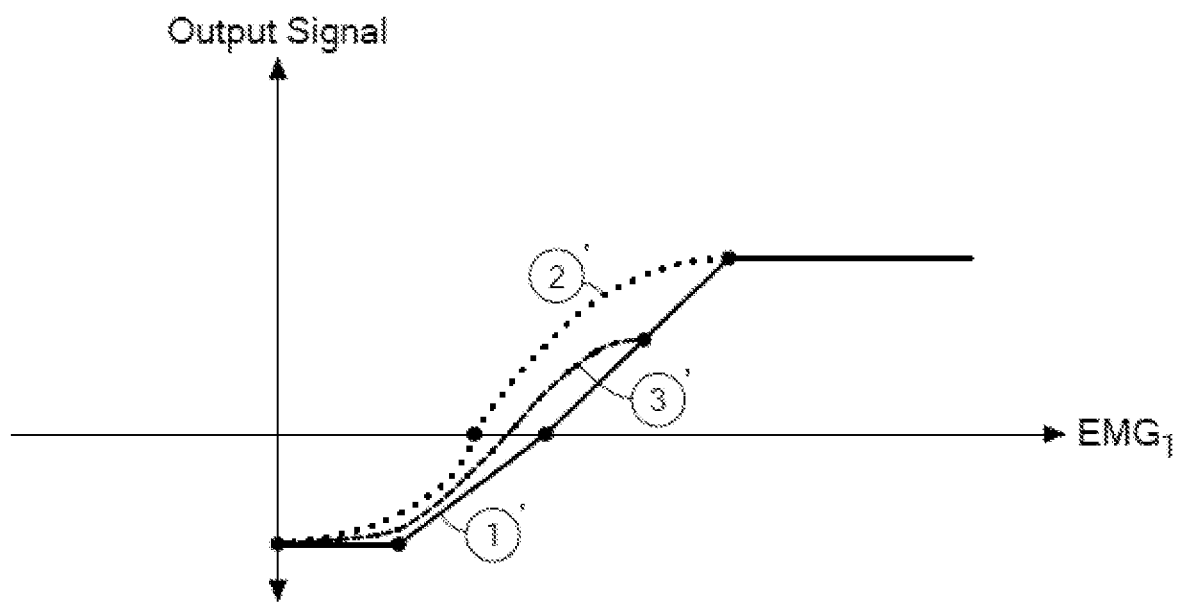

FIG. 24 shows a graph depicting features of another control algorithm. As shown, there may be hysteresis in the relationship between output signal and EMG1. The relationship may follow a certain path if EMG1 is increasing, and may follow a different path if EMG1 is decreasing. For example, the output signal may follow curve (1') if EMG1 is increasing, and the output signal may follow curve (2') if EMG1 is decreasing. Alternatively, the output signal may follow a hysteretic path (3') which departs directly from the "EMG1 increasing" or "EMG1 decreasing" curve, when EMG1 changes direction (rather than making a discontinuous jump from one curve to another, as in (2')).

Figure 25:
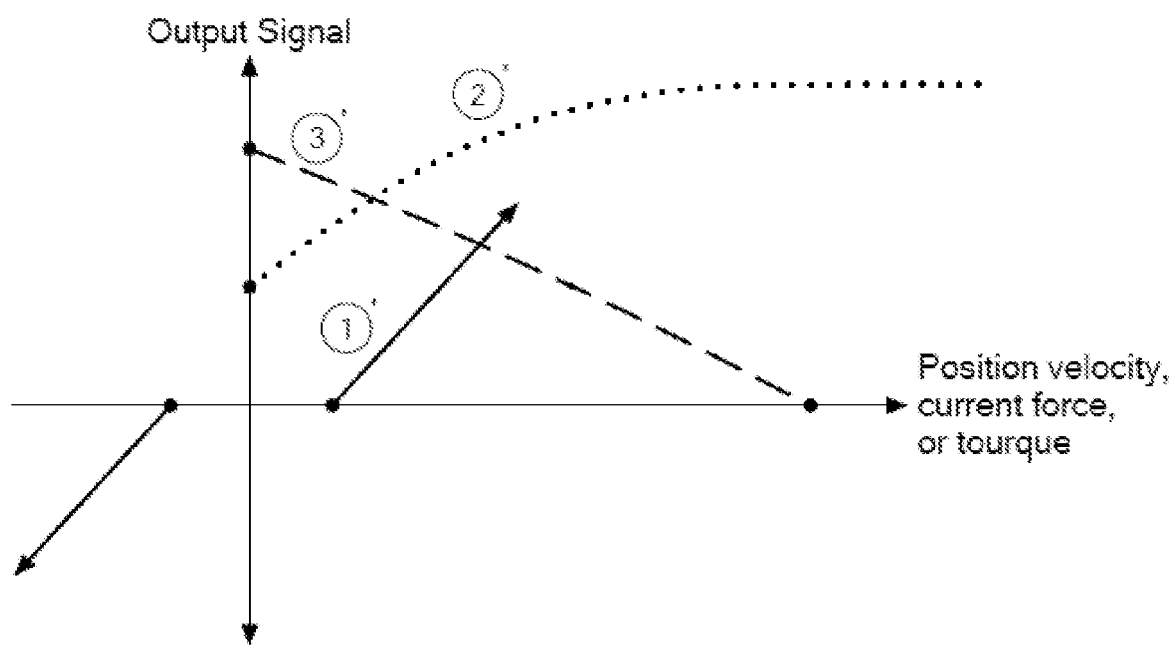
FIG. 25 shows a graph of other parameters vs. output signal according to exemplary embodiments of the present invention.

FIG. 25 shows a graph depicting features of another control algorithm, showing the potential relationship between a control output signal and other measured parameters such as joint position, joint velocity, current and various measured forces or torques. As shown, the relationships may be linear (1') or non-linear (2', 3'), increasing or decreasing (3') or both. The relationship may be continuous or discontinuous (1'), and may have positive and negative components. The relationship may also be asymptotic, and may have saturation limits (2').

Figure 26:
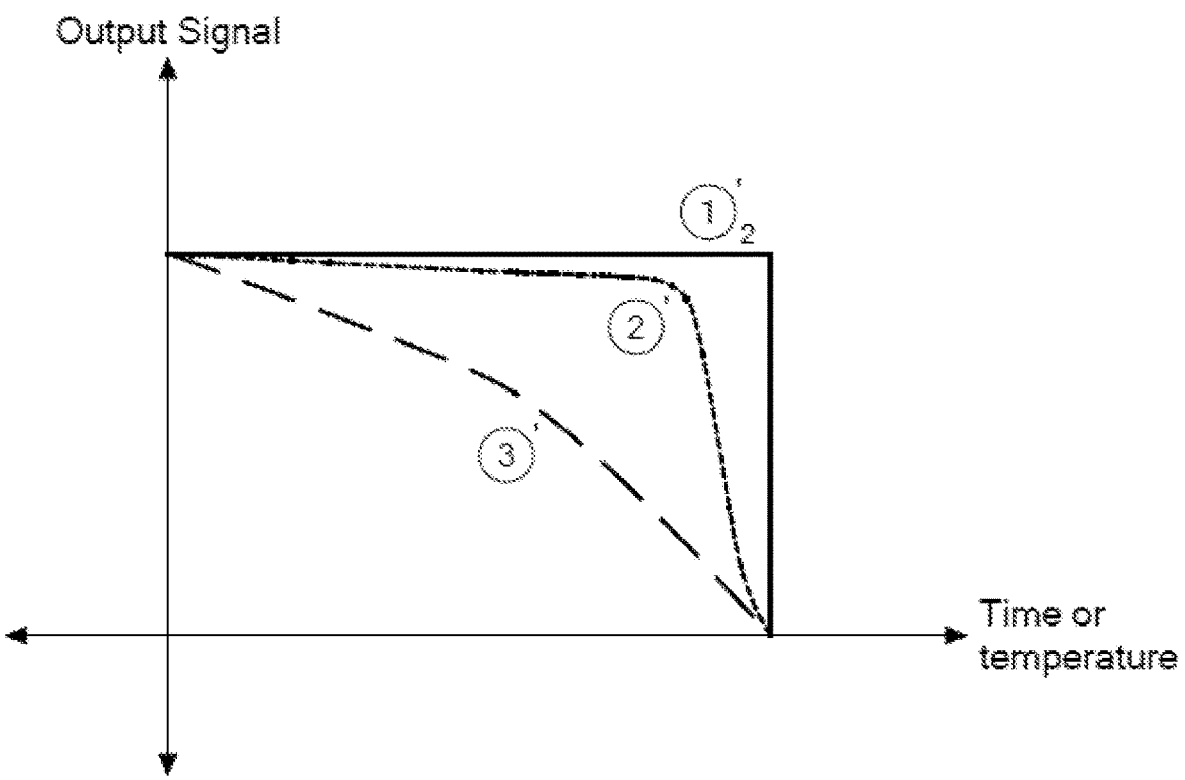
FIG. 26 shows a graph of time or temperature parameters vs. output signal according to exemplary embodiments of the present invention.

FIG. 26 shows a graph depicting features of another control algorithm, showing the potential relationship between a control output signal and other measured or unmeasured parameters such as temperature or time. As shown, the relationship may be linear or non-linear (1', 2', 3'), increasing or decreasing (3') or both. The relationship may be continuous or discontinuous (1'), and may have positive and negative components. The relationship may also be asymptotic, and may have saturation limits (2'). They may have regions of zero slope, and regions of infinite slope (1').

Figure 27:
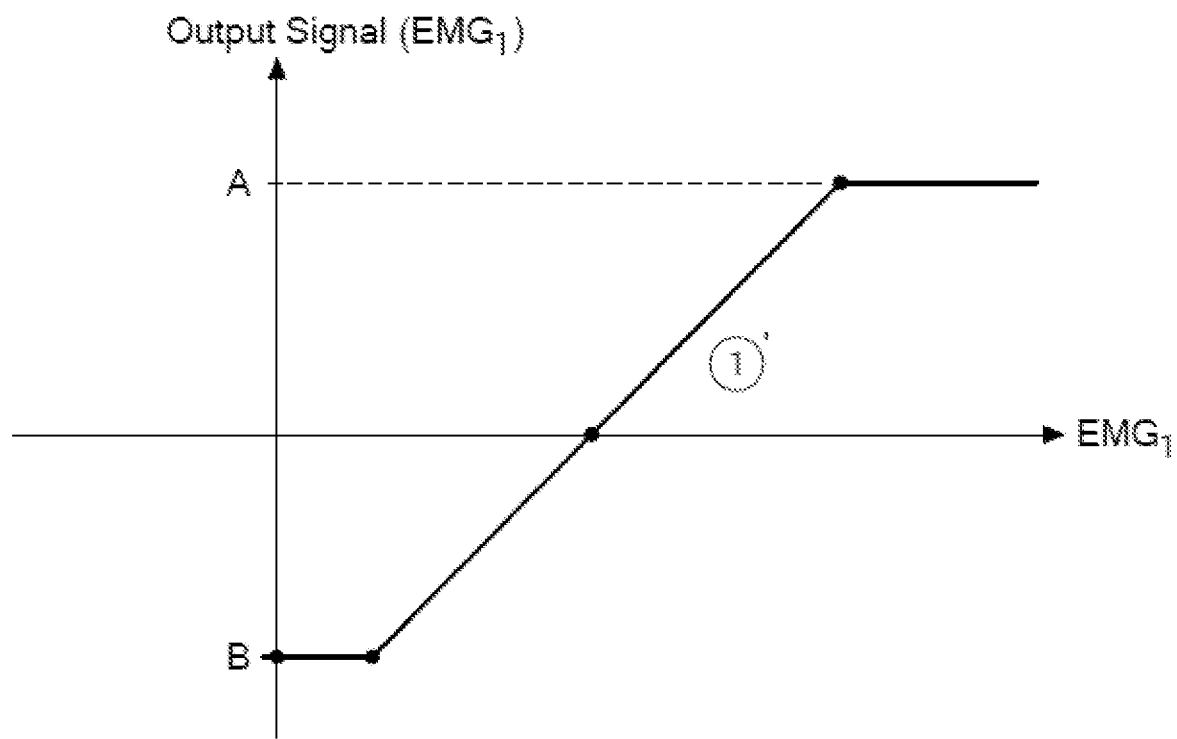
FIG. 27 shows a graph of EMG signal vs. output signal according to exemplary embodiments of the present invention.
Figure 28:
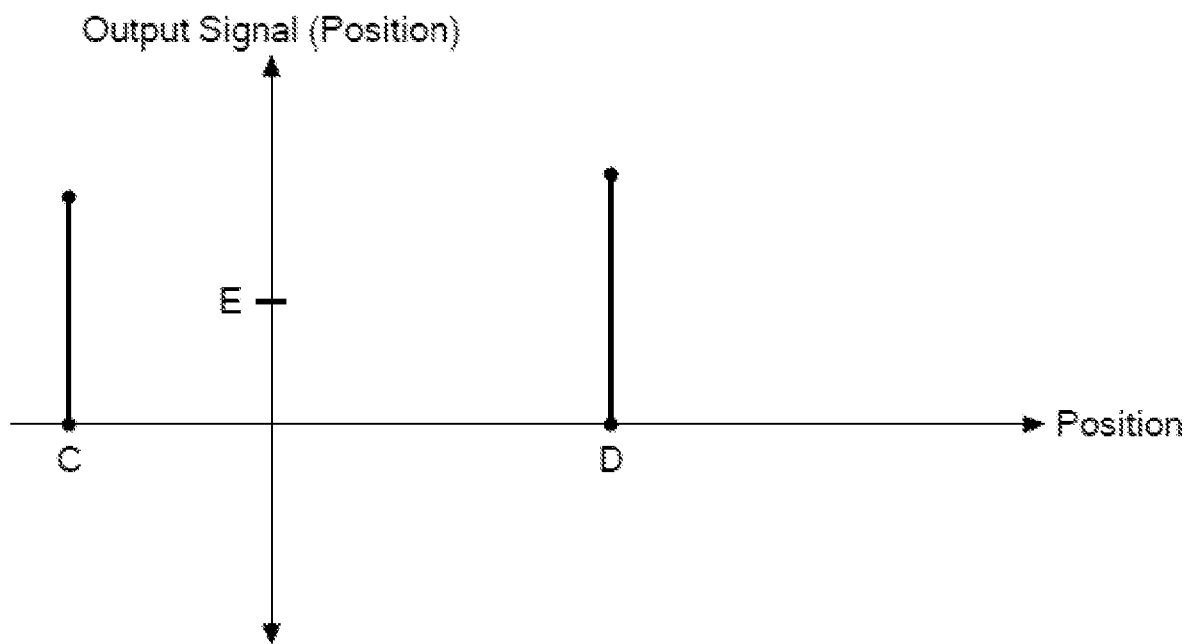
FIG. 28 shows a graph of position vs. output signal according to exemplary embodiments of the present invention.
Figure 29:
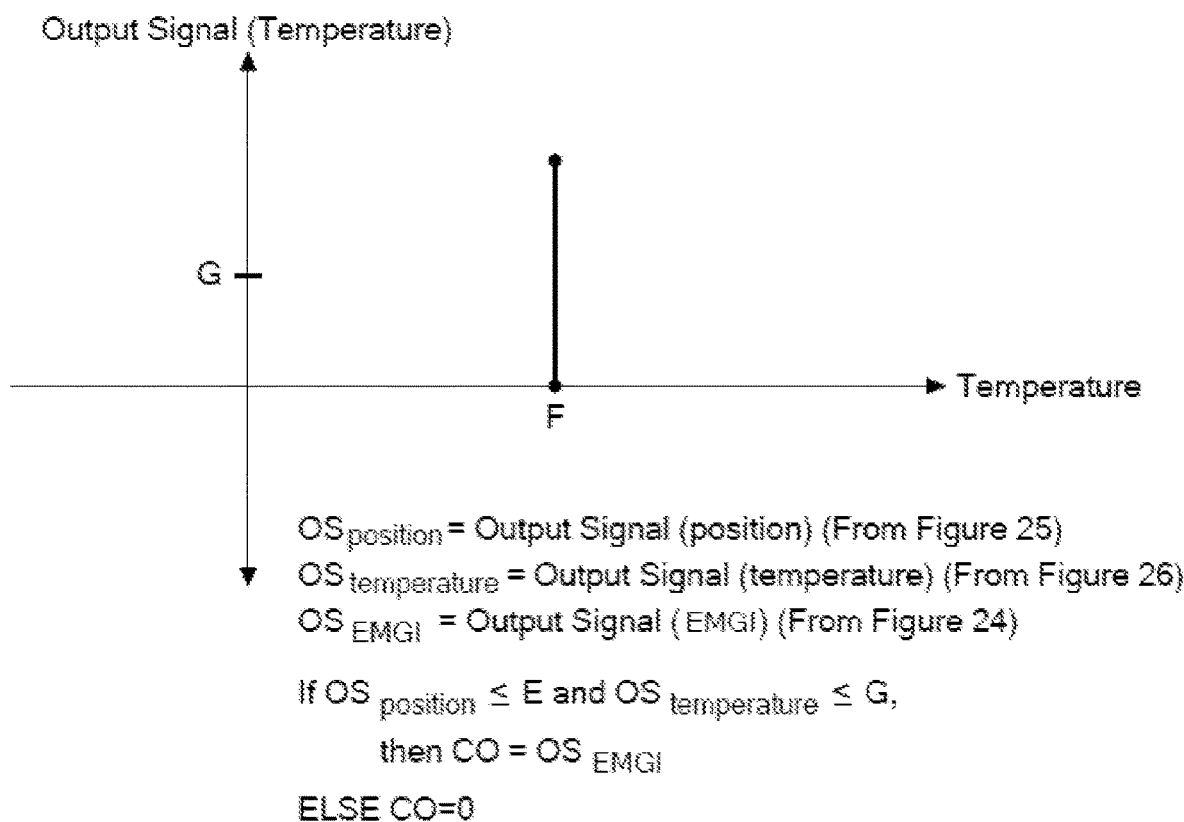
FIG. 29 shows a graph of temperature vs. output signal and a control algorithm according to exemplary embodiments of the present invention.

FIGS. 27-29 show graphs depicting features of a control algorithm. The equation for the command output to the actuator assembly 130, 165 is shown in FIG. 29. As shown, the slope of the line (1'), and the values of the constants (A, B, C, D, E, F, G) are adjustable via the user interface.

Any of the control algorithms described herein may be adjusted based on the output of the IMU 180. For example, when the IMU 180 detects that the user has lowered his or her forearm, the device 100 may operate according to the default control algorithm(s). However, once the user raises his or her forearm, the device 100 may change one or more slopes in the control algorithm(s). Since the user may wish to maintain his or her forearm in an upright position, but have difficulty doing so as a result of their impaired muscle control, the device 100 may require stronger signals from the EMG sensors 120, 121 before the device 100 will lower the user's forearm. The device 100 may similarly increase slope(s) in the control algorithm(s) when the IMU 180 output indicates that the user has lifted his or her upper arm.

Other Features of or Used with, the Powered Orthotic Device

In the embodiments depicted in FIGS. 1-15, the first and second sections 114, 116 of the second brace sub-assembly 110 are configured to be removably detached to the user's fingers and thumb. Although these embodiments drive the second brace sub-assembly 110 to move the user's fingers and thumb to effect radial and ulnar deviation, in other embodiments, the first and second sections 114, 116 may be configured to be removably detached to other limb segments, or the same limb segment, so that the second brace sub-assembly 110 operates with respect to different joints and achieves different types of motion.

For example, the first section 114 may be configured to be attached to the user's hand, and the second section 116 may be configured to be attached to the user's forearm. In this manner, the second brace sub-assembly 110 may operate with respect to a joint in the user's wrist. Based on the EMG sensors 120, 121 and/or the IMU 180, the actuator assembly may drive the first and second sections 114, 116 to move to effect flexion and extension in the user's wrist.

In another example, the first and second sections 114, 116 may be configured to be attached to the same limb segment, and the first section 114 may be configured to rotate relative to the second section 116. For example, the cuff 111 shown in FIG. 1 may be removably attachable to a user's wrist. An outer, second section 116 of the cuff 111 may be attached to the second section 155 of the first brace sub-assembly 150 in a fixed manner, and an inner, first section 114 may rotate relative to the outer, second section 116. In this manner, the second brace sub-assembly 110 may operate with respect to a different joint in the user's wrist. In this embodiment, based on the EMG sensors 120, 121 and/or the IMU 180, the actuator assembly may drive the first section 114 to rotate relative to the second section 116 to effect pronation and supination around the user's wrist.

In various embodiments, the orthotic device 100 may include multiple brace sub-assemblies, and each brace sub-assembly may operate with respect to a different joint on the user's limb. For example, a single device may include one brace sub-assembly that achieves flexion and extension between the user's upper arm and forearm, another brace sub-assembly that achieves flexion and extension between the user's forearm and hand, another brace sub-assembly that achieves pronation and supination around the user's wrist, and a final brace sub-assembly that achieves radial and ulnar deviation for a user's fingers. In these devices, brace sub-assemblies may share sections. For example, a single section may be removably attached to the user's forearm, but this section may belong to the brace sub-assembly achieving flexion and extension between the user's upper arm and forearm, and the brace sub-assembly achieving the same type of motion between the user's forearm and hand.

Embodiments depicted in the figures show cable systems coupling the controller system 167 to the first and/or second brace sub-assemblies 150, 110 using cables. However, the controller system 167 and first and/or second brace sub-assemblies 150, 110 may be configured to communicate via wireless systems.

Although the embodiments described herein include EMG sensors and/or IMUs attached to the straps 124 or 157, in some embodiments, the orthotic device 100 may not include any sensors at all. Instead, EMG sensors, IMUs, or any other type of sensor may be implanted in a user, and the orthotic device 100 may include at least one receiver that receives signals from the implanted sensor. For example, a user may have an EMG sensor implanted in his or her finger, and signals from this implanted sensor may be transmitted to a receiver on the second brace sub-assembly 110. In another example, a user may have an EMG sensor implanted in his or her forearm, and signals from this sensor may be transmitted to a receiver on either the first and/or second brace sub-assembly 150, 110. In some embodiments, the orthotic device 100 may include both sensors configured to be coupled to the surface of limb segments and receivers that receive signals from implanted sensors in the user. For example, the orthotic device 100 may include an EMG sensor configured to be coupled to the user's forearm, as well as a receiver that receives signals from an EMG sensor implanted in the user's finger.

The orthotic device 100 may include other types of sensors, and the outputs from the sensors may be used to adjust the control algorithms described herein. Exemplary additional sensors may include kinematic sensors, RFID readers obtaining information related to environmental awareness, electroencephalographic sensors, electrocorticographical (e.g., intracranial electroencephalographical) sensors, on-nerve sensors (e.g., implantable cuff electrodes), peripheral nerve sensors, temperature sensors, humidity sensors, proximity sensors, contact sensors, and force or torque sensors.

Additionally, the controller system 167 of the orthotic device 100 may be configured to be coupled to the Internet so that the device 100 may communicate with remotely located computing devices. For example, the remotely located devices may include a data management system that stores data received from the orthotic device 100, among other sources of data. In this manner, the orthotic device 100 may be configured to transmit data about the user's performance to other computing devices.

Moreover, to determine the force to apply to the first or second brace sub-assembly 150, 110, the orthotic device 100 may receive data from other computing devices that collect data regarding the user. For example, the orthotic device 100 may receive data from applications running on the user's mobile computing devices (e.g., smartphones, smartwatches). In further examples, the orthotic device 100 may receive data from personal devices, such as activity trackers, devices with global positioning systems (GPS), or any other device that obtains information about the user's physical state or location. The orthotic device 100 may also receive data from remote data management systems. The data management system may transmit information regarding the user's own medical records and information gleaned from other patient records, and the controller system 167 may analyze this data, in conjunction with other data, to determine the force to apply to the first and/or second brace sub-assemblies 150, 110.

In some embodiments, the orthotic device 100 includes a battery. The device 100 may be configured for wired or wireless charging for the battery. For example, the device 100 may include an interface in a housing configured to receive a cable that may be plugged into an outlet. The device 100 may include an inductive coil that receives an electromagnetic field from an inductive charger and converts the power back into electrical current to charge the battery. However, any other method for charging the battery, either through wired or wireless approaches, may be used. Moreover, the device 100 may include more than one battery. In various embodiments, all of the batteries may be wirelessly charged or charged through wires. In some embodiments, a subset of the batteries may be wirelessly charged, whereas the remaining batteries may be charged via wires.

In various embodiments, any of the actuator assemblies of the device 100 may be a linear actuator assembly or a rotary actuator assembly.

In some embodiments, the powered orthotic device 100 includes motion limits coupled to one of the drive assemblies in one of the actuator assemblies. The motion limits may be configured to limit a range of motion of the first and second sections of the first or second brace sub-assembly about one of the joints. The motion limits may be provided by mechanical stops, by software controlled by input from sensors, or both.

U.S. Pat. No. 8,585,620, entitled "Powered Orthotic Device and Method of Using Same" and issued Nov. 19, 2013, describes additional features that may be used in the orthotic device 100 described herein. Some features may be directly incorporated into the device 100, whereas other features may be adapted to be used in the device 100. The contents of the application are hereby incorporated by reference in their entirety.

The embodiments of the present invention described above are intended to be merely exemplary; numerous variations and modifications will be apparent to those skilled in the art. All such variations and modifications are intended to be within the scope of the present invention as defined in any appended claims.

What is claimed is:

1. A powered orthotic device, for use in assisting in relative motion of a forearm and an upper arm of a subject, and of a thumb and a set of fingers of the subject respectively, the powered orthotic device comprising:
    a wearable brace system including first and second brace sub-assemblies,
    the first brace sub-assembly including:
        a first section adapted to be removably attached to the subject's upper arm and a second section adapted to be removably attached to the subject's forearm, the first and second sections configured for relative motion with respect to one another about an elbow of the subject; and
        a first powered actuator assembly mechanically coupled to the first brace sub-assembly so as to apply a first force for driving the first and second sections of the first brace sub-assembly to move relative to one another; and
    the second brace sub-assembly including:
        a cuff adapted to be removably attached to a wrist of the subject, a molding adapted to be positioned on a back of a hand of the subject, and first and second sections adapted to be removably attached to the thumb and the set of fingers respectively;
        a second powered actuator assembly mechanically coupled to the first and second sections to apply a second force thereto, and therefore to cause movement of the set of fingers relative to the thumb;
    the powered orthotic device further comprising a controller system, the controller system being in communication with the first and second powered actuator assemblies, the controller system configured to receive a first signal from at least one sensor selected from the group consisting of a first electromyographic sensor, a first inertial measurement unit, and combinations thereof,
    the controller system further configured to receive a second signal from at least another sensor selected from the group consisting of a second electromyographic sensor, a second inertial measurement unit, and combinations thereof; and
    the controller system configured to determine the first force based the first signal, and further configured to determine the second force based on the second signal.

2. The powered orthotic device according to claim 1, wherein the first section of the first brace sub-assembly further comprises the first electromyographic sensor.

3. The powered orthotic device according to claim 1, wherein the second section of the first brace sub-assembly further comprises the second electromyographic sensor.

4. The powered orthotic device according to claim 1, wherein the first brace sub-assembly further comprises the first inertial measurement unit.

5. The powered orthotic device according to claim 1, wherein the first force is determined by the controller system based additionally on the second signal.

6. The powered orthotic device according to claim 1, wherein the second force is determined by the controller system based additionally on the first signal.

7. The powered orthotic device according to claim 1, wherein the second powered actuator assembly is configured to be positioned along the second brace sub-assembly and proximate to the hand.

8. The powered orthotic device according to claim 1, wherein the second powered actuator assembly is configured to be positioned on the second brace sub-assembly such that the second powered actuator assembly is positioned remotely from the wrist when the powered orthotic device is adapted to be removably attached to the subject.

9. The powered orthotic device according to claim 1, wherein the first powered actuator assembly includes a motor in a housing and a drive assembly coupled to the motor and the first and second sections of the first brace sub-assembly.

10. The powered orthotic device according to claim 9, wherein the motor is positioned proximate to a juncture between the first and second sections of the first brace sub-assembly.

11. The powered orthotic device according to claim 10, wherein the juncture is proximate to an elbow when the first brace sub-assembly is configured to be removably attached to the forearm.

12. The powered orthotic device according to claim 1, wherein the second powered actuator assembly includes a motor in a housing and a drive assembly coupled to the motor and the first and second sections of the second brace sub-assembly.

13. The powered orthotic device according to claim 12, wherein the second powered actuator assembly is supported on the molding positioned on the back of the hand of the subject and the motor is positioned proximate to a finger joint of the subject when the second brace sub-assembly is adapted to be removably attached to the hand.

14. The powered orthotic device according to claim 1, wherein the second powered actuator assembly is a linear actuator assembly or a rotary actuator assembly.

15. The powered orthotic device according to claim 1, wherein the second powered actuator assembly is a cable-based actuator assembly or a tendon-based actuator assembly.

16. The powered orthotic device according to claim 1, wherein the controller system includes a user interface through which the subject interacts with the powered orthotic device.

17. The powered orthotic device according to claim 1, wherein the controller system automatically self-adjusts one or more parameters selected from the group consisting of brace strength, system gains, system sensitivities, virtual spring parameters, electromyographic threshold values, maximum and minimum torques, operational range of motion, damping parameters, user feedback modes, data logging parameters, and combinations thereof.

18. The powered orthotic device according to claim 1, wherein the controller system is coupled to the second brace sub-assembly via a cable or wireless system.

19. The powered orthotic device according to claim 1, wherein the controller system is coupled to the Internet, so that the powered orthotic device is able to communicate with a remotely located computing device.

20. The powered orthotic device according to claim 1, wherein the controller system includes a data management system for storing data received from the powered orthotic device, from the subject or both.

21. The powered orthotic device according to claim 1, wherein the wearable brace system further includes a battery coupled to the first and second powered actuator assemblies.

22. The powered orthotic device according to claim 1, wherein the second brace sub-assembly further comprises the second inertial measurement unit.

* * * * *